(12) United States Patent
Cho et al.

(10) Patent No.: US 9,902,776 B2
(45) Date of Patent: Feb. 27, 2018

(54) ANTI-EGFR ANTIBODY AND ANTI-C-MET/ANTI-EGFR BISPECIFIC ANTIBODIES COMPRISING THE SAME

(71) Applicant: Samsung Electronics Co., Ltd., Suwon-si, Gyeonggi-do (KR)

(72) Inventors: Mi Young Cho, Seoul (KR); Seung Hyun Lee, Suwon-si (KR); Kwang Ho Cheong, Seoul (KR); Young Jun Koh, Yongin-si (KR); Jung Wook Lee, Yongin-si (KR); Powei Lin, Hwaseong-si (KR); Jae Woong Hwang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 213 days.

(21) Appl. No.: 14/446,167

(22) Filed: Jul. 29, 2014

(65) Prior Publication Data

US 2015/0030599 A1    Jan. 29, 2015

(30) Foreign Application Priority Data

Jul. 29, 2013   (KR) ........................ 10-2013-0089280

(51) Int. Cl.
| | | |
|---|---|---|
| C07K 16/28 | (2006.01) | |
| A61K 39/395 | (2006.01) | |
| A61K 39/00 | (2006.01) | |

(52) U.S. Cl.
CPC .... *C07K 16/2863* (2013.01); *A61K 2039/505* (2013.01); *C07K 2317/24* (2013.01); *C07K 2317/31* (2013.01); *C07K 2317/34* (2013.01); *C07K 2317/52* (2013.01); *C07K 2317/565* (2013.01); *C07K 2317/622* (2013.01); *C07K 2317/624* (2013.01); *C07K 2317/73* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | |
|---|---|---|
| 7,226,592 B2 | 6/2007 | Kreysch |
| 8,329,173 B2 | 12/2012 | Goetsch |
| 2005/0054019 A1 | 3/2005 | Michaud et al. |
| 2006/0165685 A1 | 7/2006 | Kreysch |
| 2009/0175860 A1 | 7/2009 | Stover et al. |
| 2009/0226455 A1 | 9/2009 | Filvaroff |
| 2010/0040629 A1 | 2/2010 | Michaud et al. |
| 2010/0254988 A1 | 10/2010 | Bossenmaier et al. |
| 2010/0254989 A1 | 10/2010 | Bossenmaier et al. |
| 2010/0255010 A1 | 10/2010 | Fuh et al. |
| 2011/0195494 A1 | 8/2011 | Borges et al. |
| 2012/0121596 A1 | 5/2012 | Fuh et al. |
| 2012/0231021 A1 | 9/2012 | Kim et al. |
| 2012/0321614 A1 | 12/2012 | Michaud et al. |
| 2013/0089542 A1 | 4/2013 | Lee et al. |
| 2013/0089557 A1 | 4/2013 | Cheong et al. |
| 2013/0156772 A1 | 6/2013 | Bossenmaier et al. |
| 2013/0272957 A1 | 10/2013 | Goetsch |
| 2013/0273054 A1 | 10/2013 | Bossenmaier et al. |
| 2013/0273060 A1 | 10/2013 | Goetsch |
| 2013/0280257 A1 | 10/2013 | Goetsch |
| 2014/0010818 A1 | 1/2014 | Goetsch |
| 2014/0056899 A1 | 2/2014 | Fuh et al. |
| 2014/0086914 A1 | 3/2014 | Michaud et al. |
| 2014/0112933 A1 | 4/2014 | Lee et al. |
| 2014/0135482 A1 | 5/2014 | Bossenmaier et al. |
| 2014/0193414 A1 | 7/2014 | Fuh et al. |

FOREIGN PATENT DOCUMENTS

| | | |
|---|---|---|
| EP | 2 491 129 A2 | 8/2012 |
| KR | 2010-0044212 A | 4/2010 |
| KR | 2011-0124369 A | 11/2011 |
| KR | 2011-0126748 A | 11/2011 |
| KR | 2013-0004563 A | 1/2013 |
| KR | 2013-0037153 A | 4/2013 |
| WO | WO 2005/016382 A1 | 2/2005 |
| WO | WO 2007/126799 A2 | 11/2007 |
| WO | WO 2010/108127 A1 | 9/2010 |
| WO | WO 2010/115551 A1 | 10/2010 |
| WO | WO 2012/137993 A1 | 10/2012 |
| WO | WO 2013/051878 A2 | 4/2013 |

OTHER PUBLICATIONS

Paul, W.E. Fundamental Immunology, 3rd Edition, 1993, pp. 292-295.*
MacCallum R.M. et al, Antibody-antigen interactions: Contact analysis and binding site topography. J. Mol. Biol., 1998, vol. 262, p. 732-745.*
Casset F, et al. A peptide mimetic of an anti-CD4 monoclonal antibody by rational design. Biochemical and Biophysical Research Communications, 2003, vol. 307, p. 198-205.*
Bendig, M.M. Humanization of rodent monoclonal antibodies by CDR grafting. Methods: A Companion to Methods in Enzymology, 1995; vol. 8, p. 83-93.*
Bostrom et al., "Variants of the Antibody Herceptin That Interact with HER2 and VEGF at the Antigen Binding Site," *Science*, 323: 1610-1614 (2009).

(Continued)

*Primary Examiner* — Michael Pak
(74) *Attorney, Agent, or Firm* — Leydig, Voit & Mayer, Ltd.

(57) ABSTRACT

An anti-EGFR scFV fragment, an anti-c-Met/anti-EGFR bispecific antibody including the same, and a method of preventing and/or treating a cancer using the same are provided.

13 Claims, 15 Drawing Sheets

(2 of 15 Drawing Sheet(s) Filed in Color)

(56) References Cited

OTHER PUBLICATIONS

Schaefer et al., "A Two-in-One Antibody against HER3 and EGFR Has Superior Inhibitory Activity Compared with Monospecific Antibodies," *Cancer Cell*, 20: 472-486 (2011).
Castoldi et al., "A novel bispecific EGFR/Met antibody blocks tumor-promoting phenotypic effects induced by resistance to EGFR inhibition and has potent antitumor activity", *Oncogene*, 32: 5593-5601 (2013).
Croasdale et al., "Development of tetravalent IgG1 dual targeting IGF-1R—EGFR antibodies with potent tumor inhibition", *Archives of Biochemistry and Biophysics*, 526: 206-218 (2012).
Kim et al., "Targeting colorectal cancer with human anti-EGFR monoclonocal antibodies: focus panitumumab", *Biologies: Targets & Therapy* 2(2): 223-228 (2008).
European Patent Office, Extended Search Report in European Patent Application No. 14178992.5, dated Nov. 24, 2014, 9 pp.
Korean Intellectual Property Office International Search Report in PCT Application PCT/KR2014/006985, dated Dec. 10, 2014, 6pp.
Kong-Beltran et al., "The Sema domain of Met is necessary for receptor dimerization and activation", *Cancer Cell*, 6:75-84 (2004).
European Patent Office, Office Action in Application No. 14178992.5, dated Jan. 7, 2016, 9 pgs.

\* cited by examiner

FIG. 5
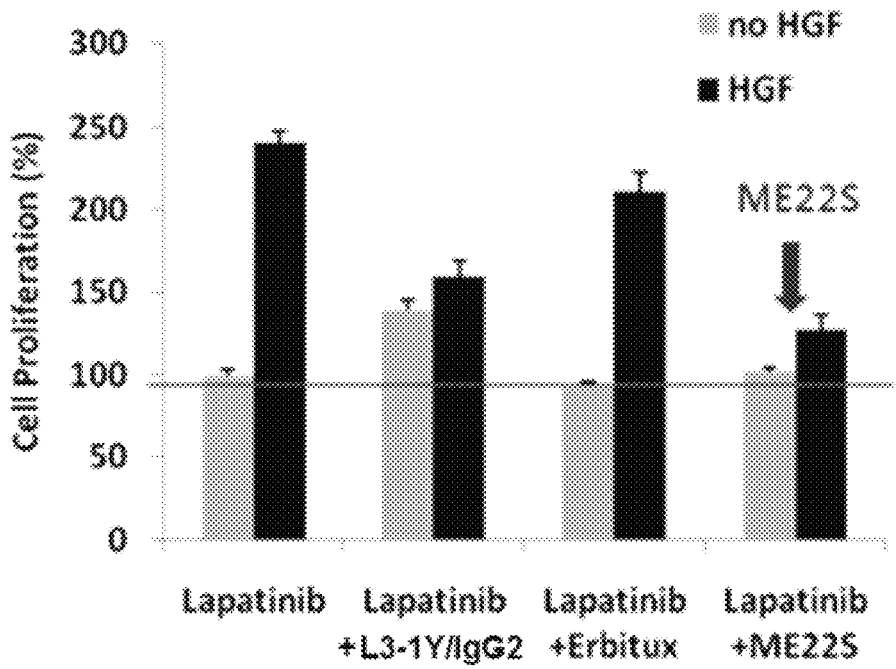
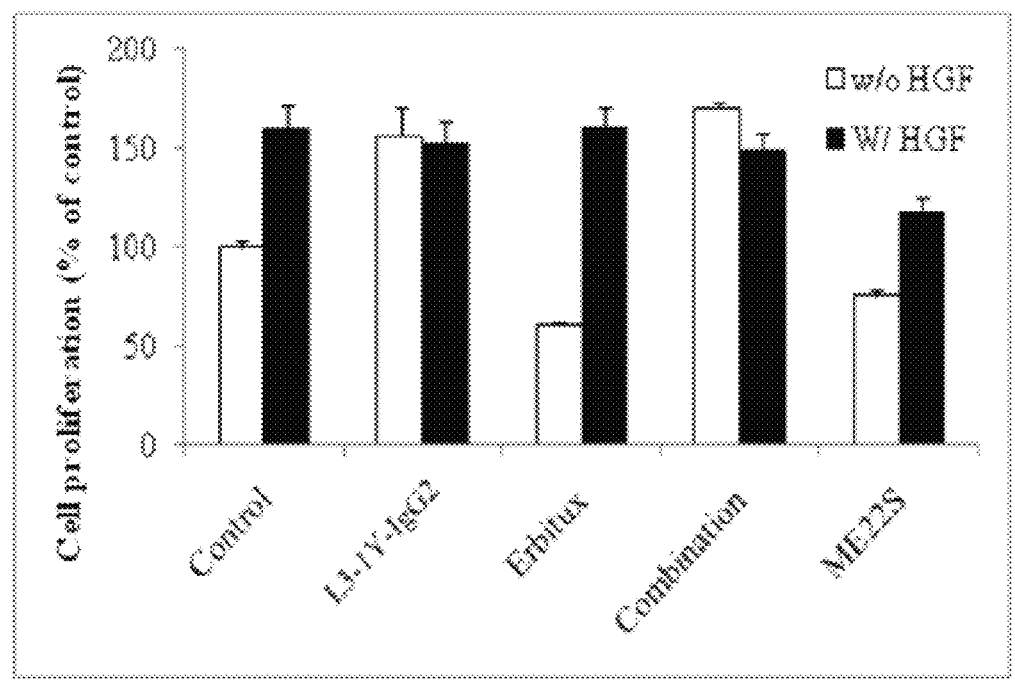

SEQUENCE LISTING

```
<160> NUMBER OF SEQ ID NOS: 121

<210> SEQ ID NO 1
<211> LENGTH: 5
<212> TYPE: PRT
<213> ORGANISM: Artificial Sequence
<220> FEATURE:
<223> OTHER INFORMATION: Synthetic (heavy chain CDR1 of AbF46)

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic (heavy chain CDR1 of c-Met antibody)
<220> FEATURE:
<221> NAME/KEY: MOD_RES
<222> LOCATION: (1)..(1)
<223> OTHER INFORMATION: Xaa is Pro or Ser or absent
<220> FEATURE:
```

```
<221> NAME/KEY: MOD_RES
<222> LOCATION: (2)..(2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: MOD_RES
<222> LOCATION: (3)..(3)
<223> OTHER INFORMATION: Xaa is Asn or Lys
<220> FEATURE:
<221> NAME/KEY: MOD_RES
<222> LOCATION: (4)..(4)
<223> OTHER INFORMATION: Xaa is Ala or Val
<220> FEATURE:
<221> NAME/KEY: MOD_RES
<222> LOCATION: (7)..(7)
<223> OTHER INFORMATION: Xaa is Asn or Thr

<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic (heavy chain CDR3 of c-Met antibody)
<220> FEATURE:
<221> NAME/KEY: MOD_RES
<222> LOCATION: (5)..(5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: MOD_RES
<222> LOCATION: (4)..(4)
<223> OTHER INFORMATION: Xaa is His, Arg, Gln or Lys
<220> FEATURE:
<221> NAME/KEY: MOD_RES
<222> LOCATION: (9)..(9)
<223> OTHER INFORMATION: Xaa is Ser or Trp
<220> FEATURE:
<221> NAME/KEY: MOD_RES
<222> LOCATION: (12)..(12)
<223> OTHER INFORMATION: Xaa is His or Gln
<220> FEATURE:
<221> NAME/KEY: MOD_RES
<222> LOCATION: (13)..(13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15
```

Ala

```
<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: MOD_RES
<222> LOCATION: (2)..(2)
<223> OTHER INFORMATION: Xaa is Ala or Gly
<220> FEATURE:
<221> NAME/KEY: MOD_RES
<222> LOCATION: (4)..(4)
<223> OTHER INFORMATION: Xaa is Thr or Lys
<220> FEATURE:
<221> NAME/KEY: MOD_RES
<222> LOCATION: (7)..(7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic (light chain CDR3 of c-Met antibody)
<220> FEATURE:
<221> NAME/KEY: MOD_RES
<222> LOCATION: (1)..(1)
<223> OTHER INFORMATION: Xaa is Gly, Ala or Gln
<220> FEATURE:
<221> NAME/KEY: MOD_RES
<222> LOCATION: (6)..(6)
<223> OTHER INFORMATION: Xaa is Arg, His, Ser, Ala, Gly or Lys
<220> FEATURE:
<221> NAME/KEY: MOD_RES
<222> LOCATION: (8)..(8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic (light chain CDR2 of AbF46)

<400> SEQUENCE: 11

Trp Ala Ser Thr Arg Val Ser
```

```
<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)

<400> SEQUENCE: 15

Ala Gln Ser Tyr Ser His Pro Phe Ser
 1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

Gln Gln Ser Tyr Ser Arg Pro Phe Thr
 1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic (heavy chain variable region of anti
      c-Met humanized antibody(huAbF46-H4))

<400> SEQUENCE: 17

Glu Val Gln Leu Val Glu Ser Gly Gly Gly Leu Val Gln Pro Gly Gly
```

```
                1               5                   10                  15
            Ser Leu Arg Leu Ser Cys Ala Ala Ser Gly Phe Thr Phe Thr Asp Tyr
                            20                  25                  30

Tyr Met Ser Trp Val Arg Gln Ala Pro Gly Lys Gly Leu Glu Trp Leu
                            35                  40                  45

Gly Phe Ile Arg Asn Lys Ala Asn Gly Tyr Thr Thr Glu Tyr Ser Ala
                            50                  55                  60

Ser Val Lys Gly Arg Phe Thr Ile Ser Arg Asp Asn Ser Lys Asn Thr
             65                 70                  75                  80

Leu Tyr Leu Gln Met Asn Ser Leu Arg Ala Glu Asp Thr Ala Val Tyr
                            85                  90                  95

Tyr Cys Ala Arg Asp Asn Trp Phe Ala Tyr Trp Gly Gln Gly Thr Leu
                            100                 105                 110

Val Thr Val Ser Ser
                            115

<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 18

Asp Ile Gln Met Thr Gln Ser Pro Ser Ser Leu Ser Ala Ser Val Gly
 1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                 70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
                100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 19

Asp Ile Gln Met Thr Gln Ser Pro Ser Ser Leu Ser Ala Ser Val Gly
 1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60
```

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
                85                  90                  95

Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic (CDR-H1 derived from YC193 clone)

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic (CDR-H3 derived from YC354 clone)

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1               5                   10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1               5                   10                  15

Ala

<210> SEQ ID NO 33
<211> LENGTH: 17
<212> TYPE: PRT
<213> ORGANISM: Artificial Sequence
<220> FEATURE:

```
<223> OTHER INFORMATION: Synthetic (CDR-L1 derived from L1-22 clone)

<400> SEQUENCE: 33

Lys Ser Ser His Ser Leu Leu Ala Ser Gly Asn Gln Asn Asn Tyr Leu
1               5                   10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-12 clone)

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of chAbF46)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
```

```
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag aaaggcact tgagtggttg gttttatta gaaacaaagc taatggttac      240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactgggc aagggactc tggtcactgt ctctgcagct      420
agcaccaagg gccatcggt cttcccctg cacctcct caagagcac tctgggggc          480
acagcggcc tgggctgcct ggtcaaggac tacttcccg aaccggtgac ggtgtcgtgg      540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct gggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416

<210> SEQ ID NO 39
<211> LENGTH: 759
<212> TYPE: DNA
<213> ORGANISM: Artificial Sequence
<220> FEATURE:
<223> OTHER INFORMATION: Synthetic (nucleotide sequence of light chain
      of chAbF46)
<220> FEATURE:
<221> NAME/KEY: misc_difference
```

```
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga aaggtcact atgagctgca agtccagtca gagtctttta      180
gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct tcccgccatc tgatgagcag     480
ttgaaatctg gaactgcctc tgttgtgtgc ctgctgaata acttctatcc cagagaggcc     540
aaagtacagt ggaaggtgga taacgccctc caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                            759

<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
65                  70                  75                  80

```
Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic (amino acid sequence of H3-heavy)

<400> SEQUENCE: 41
```

-continued

```
Glu Val Gln Leu Val Glu Ser Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

```
Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Artificial Sequence
<220> FEATURE:
```

<223> OTHER INFORMATION: Synthetic (amino acid sequence of H2-light)

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

```
Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic (nucleotide sequence of H1-heavy)
```

<400> SEQUENCE: 47

```
gaggtgcagc tggtggagtc tggggaggc ttggtccagc ctggagggtc cctgagactc      60
tcctgtgcag cctctggatt caccttcact gactactaca tgagctgggt ccgccaggct    120
ccagggaagg gctggagtg gttgggcttt attagaaaca aagctaacgg ttacaccaca    180
gaatacagtg cgtctgtgaa aggcagattc accatctcaa gagataattc aaagaactca    240
ctgtatctgc aaatgaacag cctgaaaacc gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc aagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga tgaccaag    1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa atgactcgag                                    1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48

```
gaggtgcagc tggtggagtc tggggaggc ttggtccagc ctggagggtc cctgagactc      60
tcctgtgcag cctctggatt caccttcact gactactaca tgagctgggt ccgccaggct    120
ccagggaagg gctggagtg gttgggcttt attagaaaca aagctaacgg ttacaccaca    180
gaatacagtg cgtctgtgaa aggcagattc accatctcaa gagataattc aaagaactca    240
ctgtatctgc aaatgaacag cctgcgtgct gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
```

```
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga tgaccaag     1080 aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa atgactcgag                                    1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)

<400> SEQUENCE: 49

```
gaggttcagc tggtggagtc tggcggtggc ctggtgcagc caggggggctc actccgtttg     60 tcctgtgcag cttctggctt caccttcact gattactaca tgagctgggt gcgtcaggcc    120
ccgggtaagg gcctggaatg gttgggtttt attagaaaca agctaatggt tacacaaca     180 gagtacagtg catctgtgaa gggtcgtttc actataagca gagataattc caaaaacaca    240
ctgtacctgc agatgaacag cctgcgtgct gaggacactg ccgtctatta ttgtgctaga    300
gataactggt ttgcttactg gggccaaggg actctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga tgaccaag     1080 aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
```

```
ctctccctgt ctccgggtaa atgactcgag                                      1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50

```
gacatcgtga tgacccagtc tccagactcc ctggctgtgt ctctgggcga gagggccacc      60
atcaactgca gtccagcca gagtcttta gctagcggca accaaaataa ctacttagct       120
tggcaccagc agaaaccagg acagcctcct aagatgctca ttatttgggc atctacccgg     180
gtatccgggg tccctgaccg attcagtggc agcgggtctg ggacagattt cactctcacc     240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc   480
caatcgggta actcccagga gagtgtcaca gagcaggaca gcaaggacag cacctacagc    540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                             669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic (nucleotide sequence of H2-light)

<400> SEQUENCE: 51

```
gatattgtga tgacccagac tccactctcc ctgcccgtca cccctggaga gccggcctcc     60
atctcctgca gtccagtca gagtctttta gctagtggca accaaaataa ctacttggcc     120
tggcacctgc agaagccagg gcagtctcca cagatgctga tcatttgggc atccactagg    180
gtatctggag tcccagacag gttcagtggc agtgggtcag gcactgattt cacactgaaa   240
atcagcaggg tggaggctga ggatgttgga gtttattact gccagcagtc ctacagcgct   300
ccgctcacgt tcggacaggg taccaagctg gagctcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc   480
caatcgggta actcccagga gagtgtcaca gagcaggaca gcaaggacag cacctacagc    540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                             669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic (nucleotide sequence of H3-light)

<400> SEQUENCE: 52

-continued

```
gacatcgtga tgacccagtc tccagactcc ctggctgtgt ctctgggcga gagggccacc    60
atcaactgca agtccagcca gagtctttta gctagcggca accaaaataa ctacttagct   120
tggtaccagc agaaaccagg acagcctcct aagctgctca ttatttgggc atctacccgg   180
gtatccgggg tccctgaccg attcagtggc agcgggtctg ggacagattt cactctcacc   240
atcagcagcc tgcaggctga agatgtggca gtttattact gtcagcaatc ctatagtgct   300
cctctcacgt tcggaggcgg taccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                          669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53

```
gatatccaga tgacccagtc cccgagctcc ctgtccgcct ctgtgggcga tagggtcacc    60
atcacctgca agtccagtca gagtctttta gctagtggca accaaaataa ctacttggcc   120
tggcaccaac agaaaccagg aaaagctccg aaaatgctga ttatttgggc atccactagg   180
gtatctggag tcccttctcg cttctctgga tccgggtctg ggacggattt cactctgacc   240
atcagcagtc tgcagccgga agacttcgca acttattact gtcagcagtc ctacagcgct   300
ccgctcacgt tcggacaggg taccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                          669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic (linker between VH and VL)

<400> SEQUENCE: 54

Gly Leu Gly Gly Leu Gly Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA

<213> ORGANISM: Artificial Sequence
<220> FEATURE:
<223> OTHER INFORMATION: Synthetic (polynucleotide encoding scFv of huAbF46 antibody)

<400> SEQUENCE: 55

```
gctagcgttt tagcagaagt tcaattggtt gaatctggtg gtggtttggt tcaaccaggt      60
ggttctttga gattgtcttg tgctgcttct ggttttactt tcaccgatta ttacatgtcc     120
tgggttagac aagctccagg taaaggtttg aatggttgg gtttcattag aaacaaggct      180
aacggttaca ctaccgaata ttctgcttct gttaaggta gattcaccat ttctagagac      240
aactctaaga cacccttgta cttgcaaatg aactccttga gagctgaaga tactgctgtt     300
tattactgcg ctagagataa ttggtttgct tattggggtc aaggtacttt ggttactgtt     360
tcttctggcc tcgggggcct cggaggagga ggtagtggcg gaggaggctc cggtggatcc     420
agcggtgtgg gttccgatat tcaaatgacc caatctccat cttctttgtc tgcttcagtt     480
ggtgatagag ttaccattac ttgtaagtcc tcccaatctt tgttggcttc tggtaatcag     540
aacaattact ggcttggca tcaacaaaaa ccaggtaaag ctccaaagat gttgattatt     600
tgggcttcta ccagagtttc tggtgttcca tctagatttt ctggttctgg ttccggtact     660
gattttactt tgaccatttc atccttgcaa ccagaagatt tcgctactta ctactgtcaa     720
caatcttact ctgctccatt gacttttggt caaggtacaa aggtcgaaat caagagagaa     780
ttcggtaagc ctatccctaa ccctctcctc ggtctcgatt ctacgggtgg tggtggatct     840
ggtggtggtg ttctggtgg tggtggttct caggaactga caactatatg cgagcaaatc     900
ccctcaccaa ctttagaatc gacgccgtac tctttgtcaa cgactactat tttggccaac     960
gggaaggcaa tgcaaggagt ttttgaatat acaaatcag taacgttgt cagtaattgc    1020
ggttctcacc cctcaacaac tagcaaaggc agccccataa acacacagta tgttttttga    1080
gtttaaac                                                            1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic (expression vector including polynucleotide encoding scFv of huAbF46 antibody)
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference

```
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg ttttcaata ttttctgtta ttgctagcgt tttagcagaa gttcaattgg    600
ttgaatctgg tggtggtttg gttcaaccag gtggttcttt gagattgtct tgtgctgctt    660
ctggttttac tttcaccgat tattacatgt cctgggttag acaagctcca ggtaaaggtt    720
tggaatggtt gggtttcatt agaaacaagg ctaacggtta cactaccgaa tattctgctt    780
ctgttaaggg tagattcacc atttctagag acaactctaa gaacaccttg tacttgcaaa    840
tgaactcctt gagagctgaa gatactgctg tttattactg cgctagagat aattggtttg    900
cttattgggg tcaaggtact ttggttactg tttcttctgg cctcgggggc tcggaggag    960 gaggtagtgg cggaggaggc tccggtggat ccagcggtgt gggttccgat attcaaatga   1020
cccaatctcc atcttctttg tctgcttcag ttggtgatag agttaccatt acttgtaagt   1080
cctcccaatc tttgttggct tctggtaatc agaacaatta cttggcttgg catcaacaaa   1140
aaccaggtaa agctccaaag atgttgatta tttgggcttc taccagagtt tctggtgttc   1200
catctagatt ttctggttct ggttccggta ctgattttac tttgaccatt tcatccttgc   1260
aaccagaaga tttcgctact tactactgtc aacaatctta ctctgctcca ttgacttttg   1320
gtcaaggtac aaaggtcgaa atcaagagag aattcggtaa gcctatccct aaccctctcc   1380
tcggtctcga ttctacgggt ggtggtggat ctggtggtgg tggttctggt ggtggtggtt   1440
ctcaggaact gacaactata tgcgagcaaa tcccctcacc aactttagaa tcgacgccgt   1500
actctttgtc aacgactact attttggcca acgggaaggc aatgcaagga gttttttgaat   1560 attacaaatc agtaacgttt gtcagtaatt gcggttctca cccctcaaca actagcaaag   1620
gcagccccat aaacacacag tatgtttttt gagtttaaac ccgctgatct gataacaaca   1680
gtgtagatgt aacaaaatcg actttgttcc cactgtactt ttagctcgta caaaatacaa   1740 tatactttc atttctccgt aaacaacatg ttttcccatg taatatcctt ttctattttt    1800
cgttccgtta ccaactttac acatacttta tatagctatt cacttctata cactaaaaaa   1860
```

```
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcatttttga   2040
cgaaatttgc tattttgtta gagtctttta ccaccatttgt ctccacacct ccgcttacat  2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaaagttca cctgtcccac ctgcttctga atcaaacaag ggaataaacg   2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa acatcctcc ttaggttgat    2460
tacgaaacac gccaaccaag tatttcggag tgcctgaact atttttatat gcttttacaa   2520
gacttgaaat tttccttgca ataaccgggt caattgttct ctttctattg ggcacacata   2580
taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctccttt cttttttcga ccgaatttct tgaagacgaa agggcctcgt    2820
gatacgccta ttttatagg ttaatgtcat gataataatg gtttcttagg acggatcgct    2880
tgcctgtaac ttacacgcgc ctcgtatctt ttaatgatgg ataatttggg aatttactc    2940
tgtgtttatt tattttatg ttttgtattt ggatttaga aagtaaataa agaaggtaga     3000
agagttacgg aatgaagaaa aaaaaataaa caaaggttta aaaatttca acaaaaagcg    3060
tactttacat atatatttat tagacaagaa aagcagatta aatagatata cattcgatta   3120
acgataagta aaatgtaaaa tcacaggatt ttcgtgtgtg gtcttctaca cagacaagat   3180
gaaacaattc ggcattaata cctgagagca ggaagagcaa gataaaaggt agtatttgtt   3240
ggcgatcccc ctagagtctt ttacatcttc ggaaaacaaa aactatttt tctttaattt    3300
ctttttttac tttctatttt taatttatat atttatatta aaaaatttaa attataatta   3360
tttttatagc acgtgatgaa aaggacccag gtggcacttt tcggggaaat gtgcgcggaa   3420
cccctatttg tttattttc taaatacatt caaatatgta tccgctcatg agacaataac    3480
cctgataaat gcttcaataa tattgaaaaa ggaagagtat gagtattcaa catttccgtg   3540
tcgcccttat tcccttttt gcggcatttt gccttcctgt ttttgctcac ccagaaacgc    3600
tggtgaaagt aaaagatgct gaagatcagt tgggtgcacg agtgggttac atcgaactgg   3660
atctcaacag cggtaagatc cttgagagtt ttcgccccga agaacgtttt ccaatgatga   3720
gcacttttaa agttctgcta tgtggcgcgg tattatcccg tgttgacgcc gggcaagagc   3780
aactcggtcg ccgcatacac tattctcaga atgacttggt tgagtactca ccagtcacag   3840
aaaagcatct tacggatggc atgacagtaa gagaattatg cagtgctgcc ataaccatga   3900
gtgataacac tgcggccaac ttacttctga acgatcgg aggaccgaag gagctaaccg      3960
ctttttgca caacatgggg gatcatgtaa ctcgccttga tcgttgggaa ccggagctga    4020
atgaagccat accaaacgac gagcgtgaca ccacgatgcc tgtagcaatg gcaacaacgt   4080
tgcgcaaact attaactggc gaactactta ctctagcttc ccggcaacaa ttaatagact   4140
ggatggaggc ggataaagtt gcaggaccac ttctgcgctc ggcccttccg gctggctggt   4200
ttattgctga taaatctgga gccggtgagc gtgggtctcg cggtatcatt gcagcactgg   4260
```

```
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca agtttactca tatatacttt agattgattt aaaacttcat ttttaattta    4440
aaaggatcta ggtgaagatc cttttttgata atctcatgac caaaatccct taacgtgagt    4500
tttcgttcca ctgagcgtca gaccccgtag aaaagatcaa aggatcttct tgagatcctt    4560 ttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggccgagcc tatggaaaaa cgccagcaac gcggcctttt    5160
tacggttcct ggccttttgc tggccttttg ctcacatgtt ctttcctgcg ttatccctg    5220 attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                   5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic (U6-HC7 hinge)

<400> SEQUENCE: 57

Glu Pro Lys Ser Cys Asp Cys His Cys Pro Pro Cys Pro
1               5                   10

<210> SEQ ID NO 58
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-1 clone)

<400> SEQUENCE: 58

```
gaattcacta gtgattaatt cgccgccacc atgattcac aggcccaggt cctcatgttg     60
ctgctgctat cggtatctgg tacctgtgga gatatccaga tgacccagtc cccgagctcc    120
ctgtccgcct ctgtgggcga gggtcacc atcacctgca gtccagtca gagtctttta     180 gctagtggca accaaaataa ctacttggcc tggcaccaac agaaaccagg aaaagctccg    240
```

| | |
|---|---:|
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtcagcagtc ctacagccgc ccgtacacgt tcggacaggg taccaaggtg | 420 |
| gagatcaaac gtacg | 435 |

<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-2 clone)

<400> SEQUENCE: 59

| | |
|---|---:|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtgggcagtc ctacagccgt ccgctcacgt tcggacaggg taccaaggtg | 420 |
| gagatcaaac gtacg | 435 |

<210> SEQ ID NO 60
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-3 clone)

<400> SEQUENCE: 60

| | |
|---|---:|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtgcacagtc ctacagccat ccgttctctt tcggacaggg taccaaggtg | 420 |
| gagatcaaac gtacg | 435 |

<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-5 clone)

<400> SEQUENCE: 61

| | |
|---|---:|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |

```
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                    435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, U6-HC7 hinge and constant region of human
      IgG1)

<400> SEQUENCE: 62

```
Met Glu Trp Ser Trp Val Phe Leu Val Thr Leu Leu Asn Gly Ile Gln
1               5                   10                  15

Cys Glu Val Gln Leu Val Glu Ser Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300
```

```
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
            325                 330                 335
Lys Val Ser Asn Lys Ala Leu Pro Ala Pro Ile Glu Lys Thr Ile Ser
                340                 345                 350
Lys Ala Lys Gly Gln Pro Arg Glu Pro Gln Val Tyr Thr Leu Pro Pro
        355                 360                 365
Ser Arg Glu Glu Met Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
            405                 410                 415
Gly Ser Phe Phe Leu Tyr Ser Lys Leu Thr Val Asp Lys Ser Arg Trp
                420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
450                 455                 460
```

<210> SEQ ID NO 63
<211> LENGTH: 1410
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, U6-HC7
      hinge and constant region of human IgG1)

<400> SEQUENCE: 63

```
gaattcgccg ccaccatgga atggagctgg gttttcctcg taacactttt aaatggtatc     60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc aagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc ccatcgaga aaaccatctc caaagccaaa   1080
gggcagcccc gagaaccaca ggtgtacacc ctgcccccat cccgggagga gatgaccaag   1140
```

```
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atgactcgag                                      1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region of
      human IgG1)

<400> SEQUENCE: 64

```
Met Glu Trp Ser Trp Val Phe Leu Val Thr Leu Leu Asn Gly Ile Gln
1               5                   10                  15

Cys Glu Val Gln Leu Val Glu Ser Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300
```

```
Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
        340                 345                 350

Ala Lys Gly Gln Pro Arg Glu Pro Gln Val Tyr Thr Leu Pro Pro Ser
    355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human IgG2
      hinge and constant region of human IgG1)

<400> SEQUENCE: 65
gaattcgccg ccaccatgga atggagctgg gttttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg gttttattag aaacaaagct aatggttac      240 acaacagagt acagtgcatc tgtgaagggt cgtttcacta taagcagaga taattccaaa     300
aacacactgt acctgcagat gaacagcctg cgtgctgagg acactgccgt ctattattgt     360
gctagagata ctggtttgc ttactggggc caagggactc tggtcaccgt ctcctcggct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagaggaag     720
tgctgtgtgg agtgccccc ctgcccagca cctgaactcc tggggggacc gtcagtcttc     780
ctcttccccc caaaacccaa ggacaccctc atgatctccc ggaccctga ggtcacatgc     840 gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
```

```
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc tcccgtgct ggactccgac    1260 ggctccttct tcctctacag caagctcacc gtggacaaga gcaggtggca gcagggaac    1320 gtcttctcat gctccgtgat gcatgaggct ctgcacaacc actacacgca gaagagcctc    1380
tccctgtctc cgggtaaatg actcgag                                        1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy chain of huAbF46-H4-A1, human IgG2 hinge and constant region of human IgG2)

<400> SEQUENCE: 66

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
```

```
            290                 295                 300
Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human IgG2
      hinge and constant region of human IgG2)

<400> SEQUENCE: 67
gaattcgccg ccaccatgga atggagctgg gttttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta agcagagaa taattccaaa     300 aacacactgt acctgcagat gaacagcctg cgtgctgagg acactgccgt ctattattgt     360
gctagagata ctggttttgc ttactggggc caagggactc tggtcaccgt ctcctcggct     420
agcaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccag ctgtcctaca gtcctcagga     600
ctctactccc tcagcagcgt ggtgaccgtg ccctccagca acttcggcac ccagacctac     660
acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgttgt gcaccaggac tggctgaacg gcaaggagta caagtgcaag    1020
gtctccaaca aaggcctccc agcccccatc gagaaaacca tctccaaaac caaagggcag    1080
```

```
ccccgagaac cacaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaag accacgcctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatgact cgag                                          1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1(H36Y) and human kappa constant region)

<400> SEQUENCE: 68

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: Synthetic (polynucleotide encoding polypeptide
      consisting of light chain of huAbF46-H4-A1(H36Y) and
      human kappa constant region)

<400> SEQUENCE: 69

```
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtcttttag     180
ctagtggcaa ccaaaataac tacttggcct ggtaccaaca gaaaccagga aaagctccga     240
aaatgctgat tatttgggca tccactaggg tatctgagt cccttctcgc ttctctggat      300
ccgggtctgg gacggatttc actctgacca tcagcagtct gcagccggaa gacttcgcaa     360
cttattactg tcagcagtcc tacagccgcc cgtacacgtt cggacagggt accaaggtgg     420
agatcaaacg tacggtggct gcaccatctg tcttcatctt cccgccatct gatgagcagt     480
tgaaatctgg aactgcctct gttgtgtgcc tgctgaataa cttctatccc agagaggcca     540
aagtacagtg gaaggtggat aacgccctcc aatcgggtaa ctcccaggag agtgtcacag     600
agcaggacag caaggacagc acctacagcc tcagcagcac cctgacgctg agcaaagcag     660
actacgagaa acacaaagtc tacgcctgcg aagtcaccca tcagggcctg agctcgcccg     720
tcacaaagag cttcaacagg ggagagtgtt gactcgag                             758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic (polypeptide consisting of light chain of huAbF46-H4-A1 and human kappa constant region)

<400> SEQUENCE: 70

```
Met Asp Ser Gln Ala Gln Val Leu Met Leu Leu Leu Leu Ser Val Ser
1               5                  10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
```

-continued

```
               210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic (heavy chain variable region of anti-
      c-Met antibody (AbF46 or huAbF46-H1))

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
```

-continued

```
<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of anti-
      c-Met antibody (AbF46 or huAbF46-H1))

<400> SEQUENCE: 75
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

```
<210> SEQ ID NO 76
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of anti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction sit

<400> SEQUENCE: 76
gaattcgccg ccaccatgga atggagctgg gttttctctg taacactttt aaatggtatc    60
cagtgtgagg tgaagctggt ggagtctgga ggaggcttgg tacagcctgg gggttctctg   120
```

```
agactctcct gtgcaacttc tgggttcacc ttcactgatt actacatgag ctgggtccgc    180
cagcctccag gaaaggcact tgagtggttg ggtttttatta gaaacaaagc taatggttac   240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc aagggactc tggtcactgt ctctgcagct     420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttccccccc aaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416

<210> SEQ ID NO 77
<211> LENGTH: 759
<212> TYPE: DNA
<213> ORGANISM: Artificial Sequence
<220> FEATURE:
<223> OTHER INFORMATION: Synthetic (nucleotide sequence of light chain
      of anti-c-Met antibody (AbF46 or huAbF46-H1))
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
```

<223> OTHER INFORMATION: XhoI restriction site

<400> SEQUENCE: 77

| | |
|---|---|
| gaattcacta gtgattaatt cgccgccacc atggattcac aggcccaggt cctcatgttg | 60 |
| ctgctgctat cggtatctgg tacctgtgga cattttga tgacccagtc tccatcctcc | 120 |
| ctgactgtgt cagcaggaga aaggtcact atgagctgca agtccagtca gagtcttta | 180 |
| gctagtggca accaaaataa ctacttggcc tggcaccagc agaaaccagg acgatctcct | 240 |
| aaaatgctga taatttgggc atccactagg gtatctggag tccctgatcg cttcataggc | 300 |
| agtggatctg ggacggattt cactctgacc atcaacagtg tgcaggctga agatctggct | 360 |
| gtttattact gtcagcagtc ctacagcgct ccgctcacgt tcggtgctgg gaccaagctg | 420 |
| gagctgaaac gtacggtggc tgcaccatct gtcttcatct tcccgccatc tgatgagcag | 480 |
| ttgaaatctg gaactgcctc tgttgtgtgc ctgctgaata acttctatcc cagagaggcc | 540 |
| aaagtacagt ggaaggtgga taacgccctc caatcgggta actcccagga gagtgtcaca | 600 |
| gagcaggaca gcaaggacag cacctacagc ctcagcagca ccctgacgct gagcaaagca | 660 |
| gactacgaga aacacaaagt ctacgcctgc gaagtcaccc atcagggcct gagctcgccc | 720 |
| gtcacaaaga gcttcaacag gggagagtgt tgactcgag | 759 |

<210> SEQ ID NO 78
<211> LENGTH: 4170
<212> TYPE: DNA
<213> ORGANISM: Artificial Sequence
<220> FEATURE:
<223> OTHER INFORMATION: Synthetic (polynucleotide encoding c-Met protein)

<400> SEQUENCE: 78

| | |
|---|---|
| atgaaggccc ccgctgtgct tgcacctggc atcctcgtgc tcctgtttac cttggtgcag | 60 |
| aggagcaatg gggagtgtaa agaggcacta gcaaagtccg agatgaatgt gaatatgaag | 120 |
| tatcagcttc ccaacttcac cgcggaaaca cccatccaga atgtcattct acatgagcat | 180 |
| cacattttcc ttggtgccac taactacatt tatgttttaa atgaggaaga ccttcagaag | 240 |
| gttgctgagt acaagactgg gcctgtgctg gaacacccag attgtttccc atgtcaggac | 300 |
| tgcagcagca agccaatttt atcaggaggt gtttggaaag ataacatcaa catggctcta | 360 |
| gttgtcgaca cctactatga tgatcaactc attagctgtg gcagcgtcaa cagagggacc | 420 |
| tgccagcgac atgtctttcc ccacaatcat actgctgaca tacagtcgga ggttcactgc | 480 |
| atattctccc cacagataga agagcccagc cagtgtcctg actgtgtggt gagcgccctg | 540 |
| ggagccaaag tcctttcatc tgtaaaggac cggttcatca acttctttgt aggcaatacc | 600 |
| ataaattctt cttatttccc agatcatcca ttgcattcga tatcagtgag aaggctaaag | 660 |
| gaaacgaaag atggttttat gttttttgacg gaccagtcct acattgatgt tttacctgag | 720 |
| ttcagagatt cttaccccat taagtatgtc catgcctttg aaagcaacaa ttttatttac | 780 |
| ttcttgacgg tccaaaggga aactctagat gctcagactt tcacacaag aataatcagg | 840 |
| ttctgttcca taaactctgg attgcattcc tacatggaaa tgcctctgga gtgtattctc | 900 |
| acagaaaaga gaaaaagag atccacaaag aaggaagtgt taatatact tcaggctgcg | 960 |
| tatgtcagca agcctggggc ccagcttgct agacaaatag agccagcct gaatgatgac | 1020 |
| attcttttcg gggtgttcgc acaaagcaag ccagattctg ccgaaccaat ggatcgatct | 1080 |
| gccatgtgtg cattccctat caaatatgtc aacgacttct caacaagat cgtcaacaaa | 1140 |

-continued

```
aacaatgtga gatgtctcca gcattttac ggacccaatc atgagcactg ctttaatagg      1200
acacttctga gaaattcatc aggctgtgaa gcgcgccgtg atgaatatcg aacagagttt      1260
accacagctt tgcagcgcgt tgacttattc atgggtcaat tcagcgaagt cctcttaaca      1320
tctatatcca ccttcattaa aggagacctc accatagcta atcttgggac atcagagggt      1380
cgcttcatgc aggttgtggt ttctcgatca ggaccatcaa cccctcatgt gaattttctc      1440
ctggactccc atccagtgtc tccagaagtg attgtggagc atacattaaa ccaaaatggc      1500
tacacactgg ttatcactgg gaagaagatc acgaagatcc cattgaatgg cttgggctgc      1560
agacatttcc agtcctgcag tcaatgcctc tctgccccac cctttgttca gtgtggctgg      1620
tgccacgaca aatgtgtgcg atcggaggaa tgcctgagcg ggacatggac tcaacagatc      1680
tgtctgcctg caatctacaa ggttttccca aatagtgcac cccttgaagg agggacaagg      1740
ctgaccatat gtggctggga ctttggattt cggaggaata taaatttga tttaaagaaa      1800 actagagttc tccttggaaa tgagagctgc accttgactt taagtgagag cacgatgaat      1860
acattgaaat gcacagttgg tcctgccatg aataagcatt tcaatatgtc cataattatt      1920
tcaaatggcc acgggacaac acaatacagt acattctcct atgtggatcc tgtaataaca      1980
agtatttcgc cgaaatacgg tcctatggct ggtggcactt tacttacttt aactggaaat      2040
tacctaaaca gtgggaattc tagacacatt tcaattggtg aaaaacatg tactttaaaa      2100 agtgtgtcaa acagtattct tgaatgttat accccagccc aaaccatttc aactgagttt      2160
gctgttaaat tgaaaattga cttagccaac cgagagacaa gcatcttcag ttaccgtgaa      2220
gatcccattg tctatgaaat tcatccaacc aaatctttta ttagtggtgg agcacaata      2280 acaggtgttg ggaaaaacct gaattcagtt agtgtcccga gaatggtcat aaatgtgcat      2340
gaagcaggaa ggaactttac agtggcatgt caacatcgct ctaattcaga gataatctgt      2400
tgtaccactc cttccctgca acagctgaat ctgcaactcc ccctgaaaac caaagccttt      2460
ttcatgttag atgggatcct ttccaaatac tttgatctca tttatgtaca taatcctgtg      2520
tttaagcctt ttgaaaagcc agtgatgatc tcaatgggca atgaaaatgt actggaaatt      2580
aagggaaatg atattgaccc tgaagcagtt aaaggtgaag tgttaaaagt tggaaataag      2640
agctgtgaga atatacactt acattctgaa gccgttttat gcacggtccc caatgacctg      2700
ctgaaattga acagcgagct aaatatagag tggaagcaag caatttcttc aaccgtcctt      2760
ggaaaagtaa tagttcaacc agatcagaat ttcacaggat tgattgctgg tgttgtctca      2820
atatcaacag cactgttatt actacttggg ttttttcctgt ggctgaaaaa gagaaagcaa      2880
attaaagatc tgggcagtga attagttcgc tacgatgcaa gagtacacac tcctcatttg      2940
gataggcttg taagtgcccg aagtgtaagc ccaactacag aaatggtttc aaatgaatct      3000
gtagactacc gagctacttt tccagaagat cagtttccta attcatctca gaacggttca      3060
tgccgacaag tgcagtatcc tctgacagac atgtcccca tcctaactag tggggactct      3120
gatatatcca gtccattact gcaaaatact gtccacattg acctcagtgc tctaaatcca      3180
gagctggtcc aggcagtgca gcatgtagtg attgggccca gtagcctgat tgtgcatttc      3240
aatgaagtca taggaagagg gcattttggt tgtgtatatc atgggacttt gttggacaat      3300
gatggcaaga aaattcactg tgctgtgaaa tccttgaaca gaatcactga cataggagaa      3360
gtttcccaat ttctgaccga gggaatcatc atgaaagatt ttagtcatcc caatgtcctc      3420
tcgctcctgg gaatctgcct gcgaagtgaa gggtctccgc tggtggtcct accatacatg      3480
aaacatggag atcttcgaaa tttcattcga aatgagactc ataatccaac tgtaaaagat      3540
```

```
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960 cacccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata acgctgatga tgaggtggac    4140
acacgaccag cctccttctg ggagacatca                                     4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

```
Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
```

245                 250                 255
Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
            275                 280                 285

Val Phe Ala Gln Ser Lys Pro Asp Ser Ala Glu Pro Met Asp Arg Ser
            290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
            325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
            355                 360                 365

Gln Arg Val Asp Leu Phe Met Gly Gln Phe Ser Glu Val Leu Leu Thr
            370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
            405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
            435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic (PSI-IPT domain of c-Met)

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
            35                  40                  45

Glu Glu Cys Leu Ser Gly Thr Trp Thr Gln Gln Ile Cys Leu Pro Ala
50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
            85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
            115                 120                 125

Ala Met Asn Lys His Phe Asn Met Ser Ile Ile Ile Ser Asn Gly His
            130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr 165                 170                 175
Leu Thr Gly Asn Tyr Leu Asn Ser Gly Asn Ser Arg His Ile Ser Ile
                180                 185                 190

Gly Gly Lys Thr Cys Thr Leu Lys Ser Val Ser Asn Ser Ile Leu Glu
            195                 200                 205

Cys Tyr Thr Pro Ala Gln Thr Ile Ser Thr Glu Phe Ala Val Lys Leu
        210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
                260                 265                 270

Ser Gly Gly Ser Thr Ile Thr Gly Val Gly Lys Asn Leu Asn Ser Val
            275                 280                 285

Ser Val Pro Arg Met Val Ile Asn Val His Glu Ala Gly Arg Asn Phe
        290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
                340                 345                 350

Tyr Val His Asn Pro Val Phe Lys Pro Phe Glu Lys Pro Val Met Ile
            355                 360                 365

Ser Met Gly Asn Glu Asn Val Leu Glu Ile Lys Gly Asn Asp Ile Asp
        370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
                420                 425                 430

Ile Ser Ser Thr Val Leu Gly Lys Val Ile Val Gln Pro Asp Gln Asn
            435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu

```
                65                  70                  75                  80
Pro Tyr Met Lys His Gly Asp Leu Arg Asn Phe Ile Arg Asn Glu Thr
                        85                  90                  95
His Asn Pro Thr Val Lys Asp Leu Ile Gly Phe Gly Leu Gln Val Ala
                    100                 105                 110
Lys Gly Met Lys Tyr Leu Ala Ser Lys Lys Phe Val His Arg Asp Leu
                115                 120                 125
Ala Ala Arg Asn Cys Met Leu Asp Glu Lys Phe Thr Val Lys Val Ala
            130                 135                 140
Asp Phe Gly Leu Ala Arg Asp Met Tyr Asp Lys Glu Tyr Tyr Ser Val
145                 150                 155                 160
His Asn Lys Thr Gly Ala Lys Leu Pro Val Lys Trp Met Ala Leu Glu
                165                 170                 175
Ser Leu Gln Thr Gln Lys Phe Thr Thr Lys Ser Asp Val Trp Ser Phe
                180                 185                 190
Gly Val Leu Leu Trp Glu Leu Met Thr Arg Gly Ala Pro Pro Tyr Pro
            195                 200                 205
Asp Val Asn Thr Phe Asp Ile Thr Val Tyr Leu Leu Gln Gly Arg Arg
210                 215                 220
Leu Leu Gln Pro Glu Tyr Cys Pro Asp Pro Leu Tyr Glu Val Met Leu
225                 230                 235                 240
Lys Cys Trp His Pro Lys Ala Glu Met Arg Pro Ser Phe Ser Glu Leu
                245                 250                 255
Val Ser Arg Ile Ser Ala Ile Phe Ser Thr Phe Ile Gly Glu His Tyr
                260                 265                 270
Val His Val Asn Ala Thr Tyr Val Asn Val Lys Cys Val Ala Pro Tyr
            275                 280                 285
Pro Ser Leu Leu Ser Ser Glu Asp Asn Ala Asp Asp Glu Val Asp Thr
        290                 295                 300
Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain
      of c-Met)

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc    120
ccatgtcagg actgcagcag caaagccaat ttatcaggag gtgtttggaa agataacatc    180
aacatggctc tagttgtcga cacctactat gatgatcaac tcattagctg tggcagcgtc    240
aacagaggga cctgccagcg acatgtcttt ccccacaatc atactgctga catacagtcg    300
gaggttcact gcatattctc cccacagata gaagagccca gccagtgtcc tgactgtgtg    360
gtgagcgccc tgggagccaa agtcctttca tctgtaaagg accggttcat caacttcttt    420
gtaggcaata ccataaattc ttcttatttc ccagatcatc cattgcattc gatatcagtg    480
agaaggctaa aggaaacgaa agatggtttt atgttttga cggaccagtc ctacattgat    540
gttttacctg agttcagaga ttcttacccc attaagtatg tccatgcctt tgaaagcaac    600 aatttttattt acttcttgac ggtccaaagg gaaactctag atgctcagac ttttcacaca    660
```

```
agaataatca ggttctgttc cataaactct ggattgcatt cctacatgga aatgcctctg      720
gagtgtattc tcacagaaaa gagaaaaaag agatccacaa agaaggaagt gtttaatata      780
cttcaggctg cgtatgtcag caagcctggg gcccagcttg ctagacaaat aggagccagc      840
ctgaatgatg acattctttt cggggtgttc gcacaaagca agccagattc tgccgaacca      900
atggatcgat ctgccatgtg tgcattccct atcaaatatg tcaacgactt cttcaacaag      960
atcgtcaaca aaaacaatgt gagatgtctc cagcattttt acggacccaa tcatgagcac     1020
tgctttaata ggacacttct gagaaattca tcaggctgtg aagcgcgccg tgatgaatat     1080
cgaacagagt ttaccacagc tttgcagcgc gttgacttat tcatgggtca attcagcgaa     1140
gtcctcttaa catctatatc caccttcatt aaaggagacc tcaccatagc taatcttggg     1200
acatcagagg gtcgcttcat gcaggttgtg gtttctcgat caggaccatc aacccctcat     1260
gtgaattttc tcctggactc ccatccagtg tctccagaag tgattgtgga gcatacatta     1320
aaccaaaatg gc                                                          1332

<210> SEQ ID NO 83
<211> LENGTH: 1299
<212> TYPE: DNA
<213> ORGANISM: Artificial Sequence
<220> FEATURE:
<223> OTHER INFORMATION: Synthetic (polynucleotide encoding PSI-IPT
      domain of c-Met)

<400> SEQUENCE: 83
tacacactgg ttatcactgg gaagaagatc acgaagatcc cattgaatgg cttgggctgc       60
agacatttcc agtcctgcag tcaatgcctc tctgccccac cctttgttca gtgtggctgg      120
tgccacgaca aatgtgtgcg atcggaggaa tgcctgagcg ggacatggac tcaacagatc      180
tgtctgcctg caatctacaa ggttttccca atagtgcacc ccttgaagg agggacaagg       240 ctgaccatat gtggctggga ctttggattt cggaggaata taaatttga tttaaagaaa       300 actagagttc tccttggaaa tgagagctgc accttgactt aagtgagag cacgatgaat      360 acattgaaat gcacagttgg tcctgccatg aataagcatt tcaatatgtc cataattatt       420
tcaaatggcc acgggacaac acaatacagt acattctcct atgtggatcc tgtaataaca       480
agtatttcgc cgaaatacgg tcctatggct ggtggcactt tacttacttt aactggaaat       540
tacctaaaca gtgggaattc tagacacatt tcaattggtg gaaaaacatg tactttaaaa       600
agtgtgtcaa acagtattct tgaatgttat accccagccc aaaccatttc aactgagttt       660
gctgttaaat tgaaaattga cttagccaac cgagagacaa gcatcttcag ttaccgtgaa      720
gatcccattg tctatgaaat tcatccaacc aaatctttta ttagtggtgg agcacaata       780 acaggtgttg ggaaaaacct gaattcagtt agtgtcccga gaatggtcat aaatgtgcat       840
gaagcaggaa ggaactttac agtggcatgt caacatcgct ctaattcaga gataatctgt       900
tgtaccactc cttccctgca acagctgaat ctgcaactcc ccctgaaaac caaagccttt       960
ttcatgttag atgggatcct ttccaaatac tttgatctca tttatgtaca taatcctgtg     1020
tttaagcctt ttgaaaagcc agtgatgatc tcaatgggca atgaaaatgt actgaaaatt     1080
aagggaaatg atattgaccc tgaagcagtt aaaggtgaag tgttaaaagt tggaaataag     1140
agctgtgaga atatacactt acattctgaa gccgttttat gcacggtccc caatgacctg     1200
ctgaaattga acagcgagct aaatatagag tggaagcaag caatttcttc aaccgtcctt     1260
ggaaaagtaa tagttcaacc agatcagaat ttcacagga                            1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic (polynucleotide encoding TyrKc domain
      of c-Met)

<400> SEQUENCE: 84
gtgcatttca atgaagtcat aggaagaggg cattttggtt gtgtatatca tgggactttg     60
ttggacaatg atggcaagaa aattcactgt gctgtgaaat ccttgaacag aatcactgac    120
ataggagaag tttcccaatt tctgaccgag ggaatcatca tgaaagattt tagtcatccc    180
aatgtcctct cgctcctggg aatctgcctc gaagtgaag ggtctccgct ggtggtccta    240
ccatacatga acatggaga tcttcgaaat tcattcgaa atgagactca taatccaact    300
gtaaaagatc ttattggctt tggtcttcaa gtagccaaag gcatgaaata tcttgcaagc    360
aaaaagtttg tccacagaga cttggctgca agaaactgta tgctggatga aaaattcaca    420
gtcaaggttg ctgattttgg tcttgccaga gacatgtatg ataaagaata ctatagtgta    480
cacaacaaaa caggtgcaaa gctgccagtg aagtggatgg ctttggaaag tctgcaaact    540
caaaagttta ccaccaagtc agatgtgtgg tcctttggcg tgctcctctg ggagctgatg    600
acaagaggag ccccaccta tcctgacgta acaccttg atataactgt ttacttgttg    660
caagggagaa gactcctaca acccgaatac tgcccagacc ccttatatga agtaatgcta    720
aaatgctggc accctaaagc cgaaatgcgc ccatccttt ctgaactggt gtcccggata    780
tcagcgatct tctctacttt cattggggag cactatgtcc atgtgaacgc tacttatgtg    840
aacgtaaaat gtgtcgctcc gtatccttct ctgttgtcat cagaagataa cgctgatgat    900
gaggtggaca cacgaccagc ctccttctgg gagacatca                          939

<210> SEQ ID NO 85
<211> LENGTH: 13
<212> TYPE: PRT
<213> ORGANISM: Artificial Sequence
<220> FEATURE:
<223> OTHER INFORMATION: Synthetic (heavy chain CDR3 of anti-c-Met
      antibody)

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic (heavy chain variable region of monoclonal antibody AbF46)

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody)

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 89

Gln Gln Ser Tyr Ser Ala Pro Leu Thr Phe Gly Ala Gly Thr Lys Leu
1               5                   10                  15

Glu

```
<210> SEQ ID NO 90
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH1)

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gly Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH2)

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH3)

<400> SEQUENCE: 92
```

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH4)

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH5)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
                    100                 105                 110

Val Thr Val Ser Ser
            115

<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
                    100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of AT-
      Vk1)

<400> SEQUENCE: 96

Asp Ile Leu Met Thr Gln Ser Pro Ser Ser Leu Thr Ala Ser Val Gly
 1               5                  10                  15

Asp Arg Val Thr Met Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of AT-
      Vk2)

<400> SEQUENCE: 97

Asp Ile Leu Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of AT-
      Vk3)

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:

<223> OTHER INFORMATION: Synthetic (light chain variable region of AT-Vk4)

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
                100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic (modified hinge region(U7-HC6))

<400> SEQUENCE: 100

Glu Pro Ser Cys Asp Lys His Cys Cys Pro Pro Cys Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102

Glu Arg Lys Cys Cys Val Glu Cys Pro Pro Cys Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic (modified hinge region(U6-HC8))

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 106

Lys Ser Ser Gln Ser Leu Leu Ala Trp Gly Asn Gln Asn Asn Tyr Leu
1               5                   10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic (amino acid sequence of light chain
      variable region of antibody L3-11Y)

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220

```
<212> TYPE: PRT
<213> ORGANISM: Artificial Sequence
<220> FEATURE:
<223> OTHER INFORMATION: Synthetic (amino acid sequence of light chain
      of antibody L3-11Y)

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 109
<211> LENGTH: 5
<212> TYPE: PRT
<213> ORGANISM: Artificial Sequence
<220> FEATURE:
<223> OTHER INFORMATION: Synthetic (CDR-H1 of anti-EGFR scFv)

<400> SEQUENCE: 109

Asn Tyr Asp Met Ser
1               5

<210> SEQ ID NO 110
<211> LENGTH: 17
<212> TYPE: PRT
<213> ORGANISM: Artificial Sequence
<220> FEATURE:
<223> OTHER INFORMATION: Synthetic (CDR-H2 of anti-EGFR scFv)

<400> SEQUENCE: 110

Gly Ile Ser His Ser Ser Gly Ser Lys Tyr Tyr Ala Asp Ser Val Lys
1               5                   10                  15

Gly
```

```
<210> SEQ ID NO 111
<211> LENGTH: 13
<212> TYPE: PRT
<213> ORGANISM: Artificial Sequence
<220> FEATURE:
<223> OTHER INFORMATION: Synthetic (CDR-H3 of anti-EGFR scFv)

<400> SEQUENCE: 111

Lys Asp Ala Thr Pro Arg Pro Leu Lys Pro Phe Asp Tyr
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic (CDR-L1 of anti-EGFR scFv)

<400> SEQUENCE: 112

Thr Gly Ser Ser Ser Asn Ile Gly Asn Asn Asp Val Ser
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Synthetic (CDR-L2 of anti-EGFR scFv)

<400> SEQUENCE: 113

Asp Asp Asn Lys Arg Pro Ser
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic (CDR-L3 of anti-EGFR scFv)

<400> SEQUENCE: 114

Gly Ser Trp Asp Ala Ser Leu Asn Ala
1               5

<210> SEQ ID NO 115
<211> LENGTH: 121
<212> TYPE: PRT
<213> ORGANISM: Artificial Sequence
<220> FEATURE:
<223> OTHER INFORMATION: Synthetic (Heavy chain variable region of
      anti-EGFR scFv)

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Gly Ile Ser His Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Asp Ala Thr Pro Arg Pro Leu Lys Pro Phe Asp Tyr Trp Gly
            100                 105                 110

Gln Gly Thr Leu Val Thr Val Ser Ser
        115                 120

<210> SEQ ID NO 116
<211> LENGTH: 111
<212> TYPE: PRT
<213> ORGANISM: Artificial Sequence
<220> FEATURE:
<223> OTHER INFORMATION: Synthetic (Light chain variable region of
      anti-EGFR scFv)

<400> SEQUENCE: 116

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Ala Tyr Val Phe Gly Gly Gly Thr Lys Leu Thr Val Leu Gly
            100                 105                 110

<210> SEQ ID NO 117
<211> LENGTH: 121
<212> TYPE: PRT
<213> ORGANISM: Artificial Sequence
<220> FEATURE:
<223> OTHER INFORMATION: Synthetic (heavy chain variable region of
      anti-EGFR antibody (modified))

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Cys Leu Glu Trp Val
        35                  40                  45

Ser Gly Ile Ser His Ser Ser Gly Ser Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Thr Pro Arg Pro Leu Lys Pro Phe Asp Tyr Trp Gly
            100                 105                 110

Gln Gly Thr Leu Val Thr Val Ser Ser
        115                 120

<210> SEQ ID NO 118
<211> LENGTH: 111
<212> TYPE: PRT
<213> ORGANISM: Artificial Sequence
```

```
<220> FEATURE:
<223> OTHER INFORMATION: Synthetic (light chain variable region of
      anti-EGFR antibody (modified))

<400> SEQUENCE: 118

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Asp Val Ser Trp Tyr Gln Gln Leu Pro Gly Thr Ala Pro Lys Leu Leu
            35                  40                  45

Ile Tyr Asp Asp Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Ala Tyr Val Phe Gly Cys Gly Thr Lys Leu Thr Val Leu Gly
            100                 105                 110

<210> SEQ ID NO 119
<211> LENGTH: 363
<212> TYPE: DNA
<213> ORGANISM: Artificial Sequence
<220> FEATURE:
<223> OTHER INFORMATION: Synthetic (coding nucleotide sequence of heavy
      chain variable region of anti-EGFR antibody)

<400> SEQUENCE: 119
gaggtgcagc tgttggagtc tgggggaggc ttggtacagc ctgggggtc cctgagactc      60 tcctgtgcag cctctggatt cacctttagc aattatgata tgagctgggt ccgccaggct     120
ccagggaagg gctggagtg gtctcaggg atctctcata gtagtggtag taaatattac       180
gctgattctg taaaaggtcg gttcaccatc tccagagaca attccaagaa cacgctgtat     240
ctgcaaatga acagcctgag agccgaggac acggccgtgt attactgtgc gaaagatgct    300
actccgcgtc cgctgaagcc tttcgactac tggggccagg gtacactggt caccgtgagc    360
tca                                                                   363

<210> SEQ ID NO 120
<211> LENGTH: 333
<212> TYPE: DNA
<213> ORGANISM: Artificial Sequence
<220> FEATURE:
<223> OTHER INFORMATION: Synthetic (coding nucleotide sequence of light
      chain variable region of anti-EGFR antibody)

<400> SEQUENCE: 120
cagtctgtgc tgactcagcc accctcagcg tctgggaccc ccgggcagag ggtcaccatc     60
tcttgtactg gctcttcatc taatattggc aataatgatg tctcctggta ccagcagctc    120
ccaggaacgg cccccaaact cctcatctat gatgataata gcggccaag cggggtccct     180 gaccgattct ctggctccaa atctggcacc tcagcctccc tggccatcag tgggctccgg    240
tccgaggatg aggctgatta ttactgtggt cttgggatg ctagcctgaa tgcttatgtc     300
ttcggcggag gcaccaagct gacggtccta ggc                                 333

<210> SEQ ID NO 121
<211> LENGTH: 114
<212> TYPE: PRT
```

-continued

```
<213> ORGANISM: Artificial Sequence
<220> FEATURE:
<223> OTHER INFORMATION: Synthetic (light chain variable region of anti
      c-Met antibody)

<400> SEQUENCE: 121

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg
```

ANTI-EGFR ANTIBODY AND ANTI-C-MET/ANTI-EGFR BISPECIFIC ANTIBODIES COMPRISING THE SAME

CROSS-REFERENCE TO RELATED APPLICATIONS

This application claims the benefit of Korean Patent Application No. 10-2013-0089280 filed on Jul. 29, 2013 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 144,062 bytes ASCII (Text) file named "718050_ST25_revised_20151120" created Nov. 20, 2015.

BACKGROUND

1. Field

Provided are an anti-EGFR antibody or antigen binding fragment thereof, an anti-c-Met/anti-EGFR bispecific antibody including the same, and a method of preventing and/or treating a cancer using the same.

2. Description of the Related Art c-Met and EGFR (or HER family) interact with each other and are involved in various mechanisms related to tumors. These proteins (targets) are typical receptor tyrosine kinases (RTKs) present at the surface of cells, thereby inducing the proliferation of cancer cells, the penetration of the cancer cells, angiogenesis, etc. Also, these proteins participate in each other's signal transduction systems by interacting with each other, thereby inducing resistance against each other's therapeutic agents.

Meanwhile, multispecific antibodies targeting two or more antigens have been developed in various kinds and forms and are expected as a new drug antibody having excellent therapeutic effects compared to a monoclonal antibody. Most multispecific antibodies have been developed so that their therapeutic effects on cancers can be increased by recognizing an antigen of cytotoxic cells (killer cells) and another antigen of cancer cells at the same time thus allowing the cancer cells to be killed by the cytotoxic cells. However, when considering that the research results reveal that cancer cells themselves can be mutated to proliferate and penetrate even by intracellular ligands or various antigens of the same cancer cells other than the targeted antigen, it is expected that a multispecific antibody capable of recognizing another antigen of the cancer cells as well as an antigen of the killer cells will be also useful in treating cancers.

Accordingly, there is a need for the development of a multispecific antibody which is predicted to achieve effective cancer treatment by recognizing two or more kinds of antigens in cancer cells at the same time (e.g., a bispecific antibody).

SUMMARY

One embodiment provides a polypeptide including one amino acid sequence or a combination of two or more amino acid sequences selected from the group consisting of SEQ ID NO: 109 to SEQ ID NO: 114.

Another embodiment provides an anti-EGFR antibody or an antigen-binding fragment thereof comprising or consisting essentially of at least one heavy chain complementarity determining region selected from the group consisting of CDR-H1 including the amino acid sequence of SEQ ID NO: 109, CDR-H2 including the amino acid sequence of SEQ ID NO: 110, and CDR-H3 including the amino acid sequence of SEQ ID NO: 111; at least one light chain complementarity determining region selected from the group consisting of CDR-L1 including the amino acid sequence of SEQ ID NO: 112, CDR-L2 including the amino acid sequence of SEQ ID NO: 113, and CDR-L3 including the amino acid sequence of SEQ ID NO: 114; or a combination of the at least one heavy chain complementarity determining region and the at least one light chain complementarity determining region.

Another embodiment provides an anti-c-Met/anti-EGFR bispecific antibody including an anti-c-Met antibody or an antigen-binding fragment thereof and an anti-EGFR antibody or an antigen-binding fragment thereof, wherein the anti-c-Met antibody or an antigen-binding fragment thereof specifically binds to an epitope including 5 or more contiguous amino acids within SEMA domain (SEQ ID NO: 79) of c-Met protein, and the anti-EGFR antibody or an antigen-binding fragment thereof includes at least one heavy chain complementarity determining region selected from the group consisting of CDR-H1 including the amino acid sequence of SEQ ID NO: 109, CDR-H2 including the amino acid sequence of SEQ ID NO: 110, and CDR-H3 including the amino acid sequence of SEQ ID NO: 111; at least one light chain complementarity determining region selected from the group consisting of CDR-L1 including the amino acid sequence of SEQ ID NO: 112, CDR-L2 including the amino acid sequence of SEQ ID NO: 113, and CDR-L3 including the amino acid sequence of SEQ ID NO: 114; or a combination of the at least one heavy chain complementarity determining region and the at least one light chain complementarity determining region.

Another embodiment provides a pharmaceutical composition including the polypeptide or the anti-c-Met/anti-EGFR bispecific antibody as an active ingredient.

Another embodiment provides a pharmaceutical composition for preventing and/or treating a cancer including the anti-c-Met/anti-EGFR bispecific antibody as an active ingredient.

Another embodiment provides a method of preventing and/or treating a cancer including administering a pharmaceutically effective amount of the anti-c-Met/anti-EGFR bispecific antibody to a subject in need of preventing and/or treating a cancer.

Additional compositions and methods are described in the following sections.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 is a graph displaying the cell growth of resistance-induced cells (HGF treated N87 cell (upper) and NCI-H820 cell (lower)) when treated with antibodies including an anti-c-Met/anti-EGFR bispecific antibody according to an embodiment.

DETAILED DESCRIPTION

Figure 1:
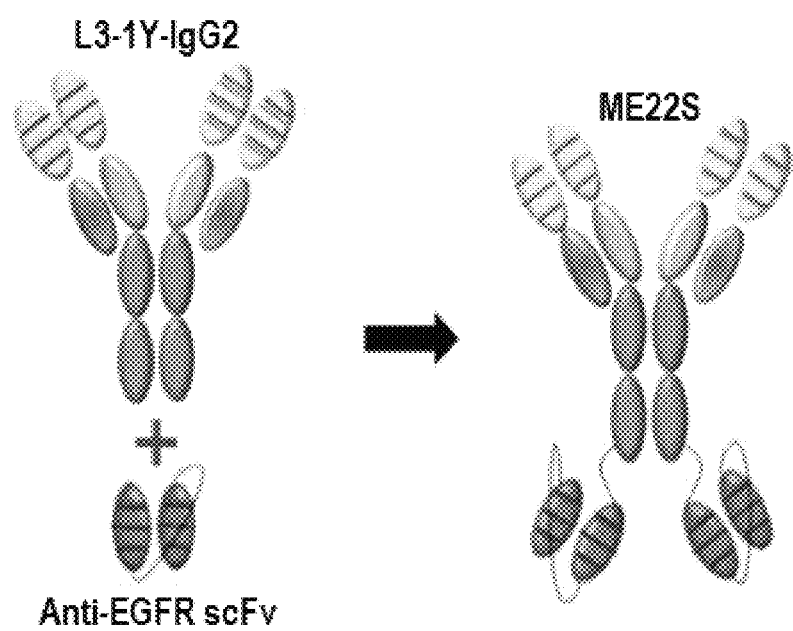
FIG. 1 is a schematic of an anti-c-Met/anti-EGFR bispecific antibody according to an embodiment.

The existing drugs which recognize only EGFR, a typical target widely expressed on cancer cells, induce over-expression and mutation of c-Met, allowing cancer cells to acquire resistance against the drugs, whereby the therapeutic effects of the drugs could be reduced. In this regard, in the present invention, it is verified that a bispecific antibody recognizing c-Met and EGFR at the same time prevents the development of resistance and shows excellent cancer cell inhibitory effects, even in cancer cells having resistance, by previously blocking c-Met-implicated signal transduction which causes resistance against drugs.

Although various bispecific antibodies have been developed, their efficiency was not proved in clinical tests or their several side effects were observed. For these reasons, there were many cases which were not approved by FDA and were not marketed as therapeutic antibodies. In spite of the fact that bispecific antibodies having various forms and mechanisms have been developed, the bispecific antibodies were not marketed due to a problem in the stability and productivity of the antibodies. In the production of early bispecific antibodies having an IgG form, due to random combination between light chains and heavy chains of antibodies, it is very difficult to separate and purify a desired kind of bispecific antibody, which becomes an obstacle in the mass production. Also, in the case of bispecific antibodies with non-IgG forms, their stabilities as a drug were not verified in protein folding, pharmacokinetics, and the like. In the present invention, it is verified that a bispecific antibody in which an anti-c-Met antibody is fused to an antibody recognizing a secondary target, EGFR, or an antigen binding fragment thereof (e.g., scFv) could improve and address the stability issue, which was the biggest problem of the pre-existing bispecific antibodies.

One embodiment provides a polypeptide including a novel amino acid sequence. The polypeptide may function as a CDR of an anti-EGFR antibody. In particular, the polypeptide may include one amino acid sequence or a combination of two or more amino acid sequences selected from the group consisting of SEQ ID NO: 109 to SEQ ID NO: 114. The function of the polypeptide including the amino acid sequence of SEQ ID NO: 109 to SEQ ID NO: 114 as a CDR of an anti-EGFR antibody is summarized in Table 1, as follows:

TABLE 1

| Heavy chain CDR | | Light chain CDR | |
|---|---|---|---|
| CDR-H1 | NYDMS (SEQ ID NO: 109) | CDR-L1 | TGSSSNIGNNDVS (SEQ ID NO: 112) |
| CDR-H2 | GISHSSGSKYYADSVKG (SEQ ID NO: 110) | CDR-L2 | DDNKRPS (SEQ ID NO: 113) |
| CDR-H3 | KDATPRPLKPFDY (SEQ ID NO: 111) | CDR-L3 | GSWDASLNA (SEQ ID NO: 114) |

In one particular embodiment, the polypeptide may a polypeptide including the amino acid sequence of SEQ ID NO: 115 or SEQ ID NO: 117, a polypeptide including the amino acid sequence of SEQ ID NO: 116 or SEQ ID NO: 118, or a combination thereof. The polypeptide including the amino acid sequence of SEQ ID NO: 115 or SEQ ID NO: 117, that includes the amino acid sequences of SEQ ID NOS: 109 to 111, and may have a function as a heavy chain variable region of an anti-EGFR antibody. In addition, the polypeptide including the amino acid sequence of SEQ ID NO: 116 or SEQ ID NO: 118, that includes the amino acid sequences of SEQ ID NOS: 112 to 114, and may have a function as a light chain variable region of an anti-EGFR antibody.

<SEQ ID NO: 115, capable of acting as a heavy chain variable region of an anti-EGFR antibody>

EVQLLESGGGLVQPGGSLRLSCAASGFTFSNYDMSWVRQAPGKGLE
                               CDR-H1

WVSGISHSSGSKYYADSVKGRFTISRDNSKNTLYLQMNSLRAEDTAVY
      CDR-H2

YCAKDATPRPLKPFDYWGQGTLVTVSS
     CDR-H3

(wherein, the CDRs are marked in bold type)
<SEQ ID NO: 116, capable of acting as a light chain variable region of an anti-EGFR antibody>

QSVLTQPPSASGTPGQRVTISCTGSSSNIGNNDVSWYQQLPGTAPKLLI
                       CDR-L1

YDDNKRPSGVPDRFSGSKSGTSASLAISGLRSEDEADYYCGSWDASL
  CDR-L2                                       CDR-L3

NAYVFGGGTKLTVLG (wherein, the CDRs are marked in bold type)
<SEQ ID NO: 117, capable of acting as a heavy chain variable region of an anti-EGFR antibody>

EVQLLESGGGLVQPGGSLRLSCAASGFTFSNYDMSWVRQAPGKCLEW
                               CDR-H1

VSGISHSSGSKYYADSVKGRFTISRDNSKNTLYLQMNSLRAEDTAVYY
     CDR-H1

CAKDATPRPLKPFDYWGQGTLVTVSS
    CDR-H1

(wherein, the CDRs are marked in bold type)
<SEQ ID NO: 118, capable of acting as a heavy chain variable region of an anti-EGFR antibody>

QSVLTQPPSASGTPGQRVTISCTGSSSNIGNNDVSWYQQLPGTAPKLLI
                       CDR-L1

YDDNKRPSGVPDRFSGSKSGTSASLAISGLRSEDEADYYCGSWDASL
  CDR-L2                                       CDR-L3

NAYVFGCGTKLTVLG (wherein, the CDRs are marked in bold type)

The polypeptide may act as a precursor or a component of an EGFR antagonist, such as an anti-EGFR antibody, an antigen-binding fragment thereof, or an anti-EGFR antibody analog (e.g., a peptibody, nanobody, etc.).

Therefore, another embodiment provides an anti-EGFR antagonist including the polypeptide. The antagonist inhibits the EGFR activity, and may be one or more selected from the group consisting of an anti-EGFR antibody, an antigen-binding fragment thereof, an anti-EGFR antibody analogue (e.g., a peptibody, nanobody, etc.), and the like.

The term "antagonist" may include any molecule capable of completely or partially preventing, inhibiting, or neutralizing one or more biological activities of a target (e.g., EGFR). For instance, an antibody as an antagonist may refer to an antibody capable of inhibiting or lowering biological activities of an antigen (e.g., EGFR) to which the antibody binds. The antagonist may bind to a receptor for a ligand (target) to decrease receptor phosphorylation, or incapacitating or killing a cell that is activated by the ligand. In addition, the antagonist may substantially decrease an interaction between a receptor and its ligand, by completely blocking the receptor-ligand interaction, binding to the receptor competitively with its ligand, or modifying or down-regulating three-dimensional structure of the receptor.

Term "peptibody (peptide+antibody)" may refer to a fusion protein wherein a peptide is fused with the whole or a part of a constant region of an antibody, such as Fc region, and the peptide acts as an antigen-binding region (e.g., a CDR or variable region of a heavy chain and/or light chain), thereby having a structure and functions similar to an antibody.

Term "nanobody" that is also called as a single-domain antibody, may refer to an antibody fragment including a single variable domain in a monomeric form and selectively binding to a specific antigen, similarly to an antibody in a complete form. The nanobody usually has a molecular weight of about 12 kDa to about 15 kDa, which is much smaller than an general molecular weight (about 150 kDa to about 160 kDa) of an antibody in a complete form (including two heavy chains and two light chains), and in some case, smaller than a molecular weight of a Fab fragment or a scFv fragment.

In a particular embodiment, the polypeptide may act as a precursor or a component of an anti-EGFR antibody.

Another embodiment provides an anti-EGFR antibody or an antigen-binding fragment thereof including the polypeptide. The antigen-binding fragment may be selected from the group consisting of scFv, (scFv)2, scFv-Fc, Fab, Fab' and F(ab')2.

In particular, the anti-EGFR antibody or an antigen-binding fragment thereof may comprise or consist essentially of:

at least one heavy chain complementarity determining region selected from the group consisting of CDR-H1 including the amino acid sequence of SEQ ID NO: 109, CDR-H2 including the amino acid sequence of SEQ ID NO: 110, and CDR-H3 including the amino acid sequence of SEQ ID NO: 111, or a heavy chain variable region including the at least one heavy chain complementarity determining region;

at least one light chain complementarity determining region selected from the group consisting of CDR-L1 including the amino acid sequence of SEQ ID NO: 112, CDR-L2 including the amino acid sequence of SEQ ID NO: 113, and CDR-L3 including the amino acid sequence of SEQ ID NO: 114 or a light chain variable region including the at least one light chain complementarity determining region;

a combination of the at least one heavy chain complementarity determining region and the at least one light chain complementarity determining region; or a combination of the heavy chain variable region and the light chain variable region.

For example, the anti-EGFR antibody or an antigen-binding fragment thereof may comprise or consisting essentially of a heavy chain variable region including the amino acid sequence of SEQ ID NO: 115 or SEQ ID NO: 117, a light chain variable region including the amino acid sequence of SEQ ID NO: 116 or SEQ ID NO: 118, or a combination thereof.

In a particular embodiment, the anti-EGFR antibody or an antigen-binding fragment thereof may be an anti-EGFR scFv comprising or consisting essentially of a heavy chain variable region including the amino acid sequence of SEQ ID NO: 115 or SEQ ID NO: 117, and a light chain variable region including the amino acid sequence of SEQ ID NO: 116 or SEQ ID NO: 118.

In the polypeptide or an anti-EGFR scFv comprising or consisting essentially of a heavy chain variable region including the amino acid sequence of SEQ ID NO: 115 or SEQ ID NO: 117, and a light chain variable region including the amino acid sequence of SEQ ID NO: 116 or SEQ ID NO: 118, the heavy chain variable region and the light chain variable region may be linked with or without a linker (e.g., a peptide linker). The peptide linker may be those including any amino acids of 1 to 100, particularly 2 to 50, and any kinds of amino acids may be included without any restrictions. The peptide linker may include for example, Gly, Asn and/or Ser residues, and also include neutral amino acids such as Thr and/or Ala. Amino acid sequences suitable for the peptide linker may be those known in the relevant art. Meanwhile, a length of the peptide linker may be variously determined within such a limit that the functions of the fusion protein will not be affected. For instance, the peptide linker may be formed by including a total of about 1 to about 100, about 2 to about 50, or about 5 to about 25 of one or more selected from the group consisting of Gly, Asn, Ser, Thr, and Ala. In one embodiment, the peptide linker may be represented as GGGGS$_n$ (n is an integer of about 1 to about 10, particularly an integer of about 2 to about 5).

As used herein, the term "antibody" may refer to a substance generated by a stimulation of an antigen in immune system, and there is no specific limitation in its kinds. The antibody may include all of an animal antibody, a chimeric antibody, a humanized antibody, and a human antibody. In addition the antibody may include an antigen-binding fragment derived from an antibody having an antigen binding affinity. The "complementarity-determining region (CDR)" may refer to a region within a variable region, which give a binding specificity to an antigen. The antigen-binding fragment as described above may be an antibody fragment including at least one complementarity-determining region, for example, one or more selected from the group consisting of scFv, (scFv)2, scFv-Fc, Fab, Fab', and F(ab')2.

In the anti-EGFR antibody or an antigen-binding fragment thereof, the rest portion of the light chain and the heavy chain portion excluding the CDRs, the light chain variable region, and the heavy chain variable region as defined above, e.g., a light chain constant region and a heavy chain constant region, may be those from any subtype of immunoglobulin (e.g., IgA, IgD, IgE, IgG (IgG1, IgG2, IgG3, IgG4), IgM, and the like).

Based on the ability of specifically binding to EGFR, the anti-EGFR antibody or an antigen-binding fragment thereof may be used in detecting EGFR or confirming activation and/or overproduction (i.e. overexpression) of EGFR.

One embodiment provides a composition for detecting the presence of EGFR including the anti-EGFR antibody or an antigen-binding fragment thereof. Another embodiment provides a method of detecting EGFR including treating a biological sample with the anti-EGFR antibody or an antigen-binding fragment thereof and detecting an antigen-antibody reaction (binding). In the method of detecting, when an antigen-antibody reaction is detected, it can be determined that EGFR is present in the biological sample. Another embodiment provides a use of the anti-EGFR antibody or an antigen-binding fragment thereof for detecting EGFR. The biological sample may be selected from the group consisting of a cell, a tissue, a body fluid (e.g., blood, serum, etc.), and the like derived from a mammal including primates such as a human, a monkey, and the like, or a rodent such as a mouse, a rat, and the like. The biological sample may be separated from a living body. The detection of EGFR may refer to detection of presence EGFR, expression of EGFR, or the level of EGFR.

Another embodiment provides a pharmaceutical composition for diagnosing activation and/or overproduction of EGFR or a disease associated with activation and/or overproduction of EGFR including the anti-EGFR antibody or an antigen-binding fragment thereof. Another embodiment provides a method of diagnosing (or determining) activation and/or overproduction of EGFR or a disease associated with activation and/or overproduction of EGFR, including treating a biological sample derived from a patient with the anti-EGFR antibody or an antigen-binding fragment thereof, and measuring a level of an antigen-antibody reaction. In this method, when the level of the antigen-antibody reaction in the biological sample is higher than that of a normal sample, the patient from which the biological sample is derived may be determined as having activation and/or overproduction of EGFR or a disease associated with activation and/or overproduction of EGFR. Therefore, the method may further include treating a normal sample with the anti-EGFR antibody or an antigen-binding fragment thereof, and measuring a level of an antigen-antibody reaction.

The biological sample may be at least one selected from the group consisting of a cell, a tissue, fluid (e.g., blood, serum, and the like) and the like, derived from a patient to be diagnosed. The biological sample may be separated from a living body. The normal sample may be at least one selected from the group consisting of a cell, a tissue, fluid (e.g., blood, serum, and the like) and the like, derived from a patient having no condition of activation and/or overproduction of EGFR or a disease associated with activation and/or overproduction of EGFR. The normal sample may be separated from a living body. The patient may be selected from a mammal, including primates such as a human, a monkey, and the like, and rodents such as a mouse, a rat, and the like.

Another embodiment provides an anti-c-Met/anti-EGFR bispecific antibody including an anti-c-Met antibody or an antigen-binding fragment thereof and an anti-EGFR antibody or an antigen-binding fragment thereof. The antigen-binding fragment thereof may be selected from the group consisting of scFv, (scFv)2, scFvFc, Fab, Fab', and F(ab')2.

The "c-Met protein" refers to a receptor tyrosine kinase binding to hepatocyte growth factor. The c-Met proteins may be derived from any species, for example, those derived from primates such as human c-Met (e.g., NP_000236) and monkey c-Met (e.g., *Macaca mulatta*, NP_001162100), or those derived from rodents such as mouse c-Met (e.g., NP_032617.2) and rat c-Met (e.g., NP_113705.1). The proteins include, for example, a polypeptide encoded by the nucleotide sequence deposited under GenBank Accession Number NM_000245, or a protein encoded by the polypeptide sequence deposited under GenBank Accession Number NM_000236, or extracellular domains thereof. The receptor tyrosine kinase c-Met is involved in several mechanisms including cancer incidence, cancer metastasis, cancer cell migration, cancer cell penetration, angiogenesis, etc.

The "EGFR (epidermal growth factor receptor)" is a member of the receptor tyrosine kinases (RTKs) of HER family. The binding of a ligand to the extracellular domain of EGFR induces receptor homo- or hetero dimerization with other ErbB receptors, which in turn results in intracellular self-phosphorylation of specific tyrosine residues. EGFR self-phosphorylation leads to downstream signal transduction networks including MAPK and PI3K/Akt activation which affects cell proliferation, angiogenesis and metastasis. Over-expression, gene amplification, mutation, or rearrangement of EGFR are frequently observed in several human malignant tumors and are related to poor prognosis of cancer treatment and bad clinical outcomes. For such reasons, the EGFR becomes an important target in anticancer therapy. The EGFR or HER2 may be derived from mammals, for example, primates such as humans and monkeys, or rodents such as rats and mice. For instance, the EGFR may be polypeptides encoded by the nucleotide sequences (mRNA) deposited under GenBank Accession Nos. JQ739160, JQ739161, JQ739162, JQ739163, JQ739164, JQ739165, JQ739166, JQ739167, NM_005228.3, NM_201284.1, NM_201282.1, or NM_201283.1.

In one embodiment, the anti-c-Met/anti-EGFR bispecific antibody may include an anti-c-Met antibody or an antigen binding fragment thereof, and an anti-EGFR antibody or an antigen binding fragment thereof which is linked to the C terminus or N terminus, for example, C terminal, of the anti-c-Met antibody or the antigen binding fragment thereof.

In the anti-c-Met/anti-EGFR bispecific antibody, in order to fully perform the anti-c-Met antibody's activity to mediate intracellular migration and degradation of c-Met proteins, it may be advantageous that the anti-c-Met antibody has its own intact antibody structure. In addition, in case of the anti-EGFR antibody, its specific recognition and binding to EGFR is important, and thus it will be fine that just an antigen-binding fragment recognizing EGFR is included in the bispecific antibody. Therefore, the anti-c-Met/anti-EGFR bispecific antibody may be those including a complete form of an anti-c-Met antibody (e.g., IgG type antibody) and an antigen binding fragment of the anti-EGFR antibody linked to the C terminus of the anti-c-Met antibody.

In the anti-c-Met/anti-EGFR bispecific antibody, the anti-c-Met antibody or the antigen binding fragment thereof, and the anti-EGFR antibody or the antigen binding fragment thereof, may be linked via a peptide linker, or they may be linked directly and without a linker. Furthermore, a heavy chain portion and a light chain portion within the antigen binding fragment, for example, a heavy chain variable region and a light chain variable region within the scFv fragment, may be linked via a peptide linker or without a linker. The peptide linker which links the anti-c-Met antibody or the antigen binding fragment thereof and the anti-EGFR antibody or the antigen binding fragment thereof, and the peptide linker which links the heavy chain portion and the light chain portion within the antigen binding fragment, may be identical or different. The peptide linker may be include about 1 to about 100 amino acid residues, particularly about 2 to about 50, and any kinds of amino acids may be included without any restrictions. The peptide linker may include for example, Gly, Asn and/or Ser residues, and also include neutral amino acids such as Thr and/or Ala. Amino acid sequences suitable for the peptide linker may be those known in the pertinent art. Meanwhile, a length of the peptide linker may be variously determined within such a limit that the functions of the fusion protein will not be affected. For instance, the peptide linker may be formed by including a total of about 1 to about 100, about 2 to about 50, or about 5 to about 25 of one or more selected from the group consisting of Gly, Asn, Ser, Thr, and Ala. In one embodiment, the peptide linker may be represented as $(GGGS)_n$ (n is an integer of about 1 to about 10, particularly an integer of about 2 to about 5).

In a particular embodiment, the anti-EGFR antibody or an antigen-biding fragment may comprise or consist essentially of:

at least one heavy chain complementarity determining region selected from the group consisting of CDR-H1 including the amino acid sequence of SEQ ID NO: 109, CDR-H2 including the amino acid sequence of SEQ ID NO: 110, and CDR-H3 including the amino acid sequence of SEQ ID NO: 111 or a heavy chain variable region including the at least one heavy chain complementarity determining region;

at least one light chain complementarity determining region selected from the group consisting of CDR-L1 including the amino acid sequence of SEQ ID NO: 112, CDR-L2 including the amino acid sequence of SEQ ID NO: 113, and CDR-L3 including the amino acid sequence of SEQ ID NO: 114 or a light chain variable region including the at least one light chain complementarity determining region;

a combination of the at least one heavy chain complementarity determining region and the at least one light chain complementarity determining region; or a combination of the heavy chain variable region and the light chain variable region.

For example, the anti-EGFR antibody or an antigen-binding fragment thereof may comprise or consist essentially of a heavy chain variable region including the amino acid sequence of SEQ ID NO: 115 or SEQ ID NO: 117, a light chain variable region including the amino acid sequence of SEQ ID NO: 116 or SEQ ID NO: 118, or a combination thereof.

In a particular embodiment, the anti-EGFR antibody or an antigen-binding fragment thereof may be an anti-EGFR scFv including a heavy chain variable region including the amino acid sequence of SEQ ID NO: 115 or SEQ ID NO: 117, and a light chain variable region including the amino acid sequence of SEQ ID NO: 116 or SEQ ID NO: 118.

The "antigen binding fragment" refers to a fragment of a full immunoglobulin structure including parts of the polypeptide including a portion capable of binding to an antigen. For example, it may be scFv, $(scFv)_2$, Fab, Fab', or $F(ab')_2$, but not be limited thereto. In the present invention, the antigen binding fragment may be an antibody fragment including at least one complementarity determining region, for example, selected from the group consisting of scFv, (scFv)2, scFv-Fc, Fab, Fab' and F(ab')2.

Of the antigen binding fragments, Fab is a structure having variable regions of a light chain and a heavy chain, a constant region of the light chain, and the first constant region ($C_{H1}$) of the heavy chain, and it has one antigen binding site.

Fab' is different from Fab in that it has a hinge region including one or more cysteine residues at the C-terminal of heavy chain $C_{H1}$ domain. An $F(ab')_2$ antibody is formed through disulfide bond of the cysteine residues at the hinge region of Fab'.

Fv is a minimal antibody piece having only a heavy chain variable region and light chain variable region, and a recombinant technique for producing the Fv fragment is well known in the pertinent art. Two-chain Fv may have a structure in which the heavy chain variable region is linked to the light chain variable region by a non-covalent bond, and single-chain Fv (scFv) may generally have a dimer structure as in the two-chain Fv in which the variable region of a heavy chain and the variable region of a light chain are covalently linked via a peptide linker or they are directly linked to each other at the C-terminal thereof. The peptide linker may be the same as described in the above.

The antigen binding fragments may be obtained using proteases (for example, a whole antibody is digested with papain to obtain Fab fragments, and is digested with pepsin to obtain F(ab')$_2$ fragments), and may be prepared by a genetic recombinant technique.

In a particular embodiment, the anti-c-Met/anti-EGFR bispecific antibody may be those including an anti-c-Met antibody, and scFv, (scFv)$_2$, Fab, Fab' or F(ab')$_2$, for example, scFv, of the anti-EGFR antibody linked to the C terminus of the anti-c-Met antibody. For instance, scFv, (scFv)$_2$, Fab, Fab' or F(ab')$_2$ of the anti-EGFR antibody may be those including a heavy chain variable region including the amino acid sequence of SEQ ID NO: 115 or SEQ ID NO: 117 and a light chain variable region including the amino acid sequence of SEQ ID NO: 116 or SEQ ID NO: 118.

In a particular embodiment, the anti-c-Met/anti-EGFR bispecific antibody may be those including the anti-c-Met antibody, and scFv, (scFv)$_2$, Fab, Fab' or F(ab')$_2$ of the anti-EGFR antibody including a heavy chain variable region including the amino acid sequence of SEQ ID NO: 115 or SEQ ID NO: 117 and a light chain variable region including the amino acid sequence of SEQ ID NO: 116 or SEQ ID NO: 118, linked to the C terminal of the anti-c-Met antibody.

The anti-c-Met antibody may be any one recognizing a specific region of c-Met, e.g., a specific region in the SEMA domain, as an epitope. It may be any antibody or antigen-binding fragment that acts on c-Met to induce intracellular internalization and degradation of c-Met.

c-Met, a receptor for hepatocyte growth factor(HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region including the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The region acts as an epitope for the specific anti-c-Met antibody of the present invention.

The term "epitope" as used herein, refers to an antigenic determinant, a part of an antigen recognized by an antibody. In one embodiment, the epitope may be a region including about 5 or more contiguous (consecutive or non-consecutive) amino acid residues within the SEMA domain (SEQ ID NO: 79) of c-Met protein, for instance, about 5 to about 19 contiguous amino acid residues within the amino acid sequence of SEQ ID NO: 71. For example, the epitope may be a polypeptide having about 5 to about 19 contiguous amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

Thus, the anti-c-Met antibody may specifically bind to an epitope which has about 5 to about 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may comprise or consist essentially of:

at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence having about 8-19 consecutive amino acids within SEQ ID NO: 2 including amino acid residues from the $3^{rd}$ to $10^{th}$ positions of SEQ ID NO: 2; and (c) a CDR-H3 including the amino acid sequence of SEQ ID NO: 6, SEQ ID NO: 85, or an amino acid sequence having about 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 86, or an amino acid sequence having 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I
(SEQ ID NO: 4)
Xaa$_1$-Xaa$_2$-Tyr-Tyr-Met-Ser, wherein Xaa$_1$ is absent or Pro or Ser, and Xaa$_2$ is Glu or Asp, Formula II
(SEQ ID NO: 5)
Arg-Asn-Xaa$_3$-Xaa$_4$-Asn-Gly-Xaa$_5$-Thr, wherein Xaa$_3$ is Asn or Lys, Xaa$_4$ is Ala or Val, and Xaa$_5$ is Asn or Thr, Formula III
(SEQ ID NO: 6)
Asp-Asn-Trp-Leu-Xaa$_6$-Tyr, wherein Xaa$_6$ is Ser or Thr, Formula IV
(SEQ ID NO: 7)
Lys-Ser-Ser-Xaa$_7$-Ser-Leu-Leu-Ala-Xaa$_8$-Gly-Asn-
Xaa$_9$-Xaa$_{10}$-Asn-Tyr-Leu-Ala wherein Xaa$_7$ is His, Arg, Gln, or Lys, Xaa$_8$ is Ser or Trp, Xaa$_9$ is His or Gln, and Xaa$_{10}$ is Lys or Asn, Formula V
(SEQ ID NO: 8)
Trp-Xaa$_{11}$-Ser-Xaa$_{12}$-Arg-Val-Xaa$_{13}$ wherein Xaa$_{11}$ is Ala or Gly, Xaa$_{12}$ is Thr or Lys, and Xaa$_{13}$ is Ser or Pro, and Formula VI
(SEQ ID NO: 9)
Xaa$_{14}$-Gln-Ser-Tyr-Ser-Xaa$_{15}$-Pro-Xaa$_{16}$-Thr wherein Xaa$_{14}$ is Gly, Ala, or Gln, Xaa$_{15}$ is Arg, His, Ser, Ala, Gly, or Lys, and Xaa$_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or antigen-binding fragment may include
a heavy chain variable region comprising a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85; and
a light chain variable region comprising a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be synthetic or recombinant.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100(U7-HC6), 101(U6-HC7), 102(U3-HC9), 103(U6-HC8), or 104(U8-HC5), or a hinge region including the amino acid sequence of SEQ ID NO: 105 (non-modified human hinge). In particular, the hinge region has the amino acid sequence of SEQ ID NO: 100 or 101.

In one embodiment, the anti-c-Met antibody or antigen-binding fragment may include a variable region of the heavy chain including the amino acid sequence of SEQ ID NO: 17, 74, 87, 90, 91, 92, 93, or 94, a variable region of the light chain including the amino acid sequence of SEQ ID NO: 18, 19, 20, 21, 75, 88, 95, 96, 97, 98, 99, or 107, or a combination thereof.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include all the antibodies defined in Korean Patent Publication No. 2011-0047698.

In the anti-c-Met antibody, the rest portion of the light chain and the heavy chain portion excluding the CDRs, the light chain variable region, and the heavy chain variable region as defined above, that is the light chain constant region and the heavy chain constant region, may be those from any subtype of immunoglobulin (e.g., IgA, IgD, IgE, IgG (IgG1, IgG2, IgG3, IgG4), IgM, and the like).

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 108.

According to an embodiment, the anti-c-Met antibody may include a heavy chain including the amino acid sequence from the $18^{th}$ to $460^{th}$ positions of SEQ ID NO: 66 and a light chain including the sequence from the $21^{st}$ to $240^{th}$ positions of SEQ ID NO: 68, or a heavy chain including the amino acid sequence from the $18^{th}$ to $460^{th}$ positions of SEQ ID NO: 66 and a light chain including the sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement.

The polypeptide with the amino acid sequence of SEQ ID NO: 108 is a polypeptide obtained by replacing serine at position 32 of SEQ ID NO: 108 (corresponding to position 52 of SEQ ID NO: 68, which corresponds to position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

In another embodiment, the anti-c-Met antibody may include a light chain complementarity determining region including the amino acid sequence of SEQ ID NO: 106, a light chain variable region including the amino acid sequence of SEQ ID NO: 107, or a light chain including the amino acid sequence of SEQ ID NO: 108.

The anti-c-Met/anti-EGFR bispecific antibody can not only inhibit the activity of c-Met and EGFR by the internalization and degradation activity of anti-c-Met antibody but also fundamentally block them by reducing the total amounts of c-Met and EGFR by the degradation thereof. Accordingly, the anti-c-Met/anti-EGFR bispecific antibody can obtain efficient effects even when applied to patients who have developed resistance against pre-existing anti-EGFR antibodies.

Another embodiment provides a pharmaceutical composition including the anti-EGFR antibody or an antigen-binding fragment thereof as an active ingredient. Another embodiment provides a pharmaceutical composition including the anti-c-Met/anti-EGFR bispecific antibody as an active ingredient.

In particular, another embodiment provides a pharmaceutical composition for preventing and/or treating a cancer including the anti-EGFR antibody or an antigen-binding fragment thereof as an active ingredient. Another embodiment provides a pharmaceutical composition for preventing and/or treating a cancer including the anti-c-Met/anti-EGFR bispecific antibody as an active ingredient.

Another embodiment provides a method of prevention and/or treatment a cancer, including administering a pharmaceutical effective amount of the anti-EGFR antibody or an antigen-binding fragment thereof to a patient in need of the prevention and/or treatment of the cancer. Another embodiment provides a method of prevention and/or treatment a cancer, including administering a pharmaceutical effective amount of the anti-c-Met/anti-EGFR bispecific antibody to a patient in need of the prevention and/or treatment of the cancer. The method of prevention and/or treatment a cancer may further comprises a step of identifying the patient in need of the prevention and/or treatment of the cancer, prior to the step of administering.

The cancer may be any cancer associated with overexpression and/or abnormal activation of c-Met and/or EGFR. The cancer may be any cancer in which EGFR and/or c-Met possibly plays an important role for proliferation, invasion, and metastasis, including the resistant cancers to EGFR therapy. The cancer may be a solid cancer or hematological cancer and for instance, may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, and the like. In particular, the cancer may be cancer having resistance against pre-existing anticancer drugs, for example, antagonists against EGFR and/or antagonists against c-Met. The prevention and/or treatment effects of the cancers may include effects of not only suppressing the growth of the cancer cells but also suppressing deterioration of cancers due to migration, invasion, and/or metastasis thereof. Therefore, the curable cancers may include both primary cancers and metastatic cancers. Thus, the pharmaceutical composition or method may be for preventing and/or treating cancer metastasis.

In the pharmaceutical composition or method, the pharmaceutically effective amount of the anti-EGFR antibody or an antigen-binding fragment thereof or the anti-c-Met/anti-EGFR bispecific antibody may be administered along with at least one additive selected from the group consisting of a pharmaceutically acceptable carriers, diluents, and excipients.

The pharmaceutically acceptable carrier to be included in the composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative.

The pharmaceutical composition or the anti-EGFR antibody or an antigen-binding fragment thereof or the anti-c-Met/anti-EGFR bispecific antibody may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

A suitable dosage of the pharmaceutical composition, the anti-EGFR antibody or an antigen-binding fragment thereof, or the anti-c-Met/anti-EGFR bispecific antibody may be prescribed in a variety of ways, depending on factors such as formulation methods, administration methods, age of patients, body weight, gender, pathologic conditions, diets, administration time, administration route, excretion speed, and reaction sensitivity. A desirable dosage of the pharmaceutical composition or the anti-c-Met/anti-EGFR bispecific antibody may be in the range of about 0.001 to 100 mg/kg for an adult. For example, the suitable dosage of the pharmaceutical composition, the anti-EGFR antibody or an antigen-binding fragment thereof, or the anti-c-Met/anti-EGFR bispecific antibody may be about 0.001 to about 1000 mg/kg, about 0.01 to about 100 mg/kg, or 0.1 to 50 mg/kg, per a day, but not be limited thereto. The term "pharmaceutically effective amount" used herein refers to an amount of the active ingredient (i.e., the anti-EGFR antibody or an antigen-binding fragment thereof, or the anti-c-Met/anti-EGFR bispecific antibody) exhibiting effects in preventing or treating cancer, and may be properly determined in a variety of ways, depending on factors such as formulation methods, administration methods, age of patients, body weight, gender, pathologic conditions, diets, administration time, administration route, excretion speed, and reaction sensitivity.

The pharmaceutical composition or the anti-c-Met/anti-EGFR bispecific antibody may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

In addition, the pharmaceutical composition or the anti-c-Met/anti-EGFR bispecific antibody may be administered as an individual drug, or together with other drugs, and may be administered sequentially or simultaneously with pre-existing drugs.

Since the pharmaceutical composition includes an antibody or an antigen binding fragment thereof, it may be formulated as an immunoliposome. The liposome containing an antibody may be prepared using a well-known method in the pertinent art. The immunoliposome is a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide exchange reaction. A chemical drug such as doxorubicin may be additionally included in the liposome.

The subject to which the pharmaceutical composition is administered or the patient to which the prevention and/treatment method is applied may be mammals, for example, primates such as humans and monkeys, or rodents such as rats and mice, but are not be limited thereto. The subject or the patient may be a cancer patient having resistance against pre-existing anticancer drugs, for example, antagonists against the target cell membrane proteins (e.g., EGFR).

Another embodiment provides a polynucleotide encoding a polypeptide including one amino acid sequence or a combination of two or more amino acid sequences selected from the group consisting of SEQ ID NO: 109 to SEQ ID NO: 114. In a particular embodiment, the polynucleotide may encode a polypeptide including the amino acid sequence of SEQ ID NO: 115 or SEQ ID NO: 117, a polypeptide including the amino acid sequence of SEQ ID NO: 116 or SEQ ID NO: 118, or a combination thereof. Another embodiment provides a recombinant vector including the polynucleotide. Another embodiment provides a recombinant cell transfected with the recombinant vector.

The term "vector" used herein refers to a means for expressing a target gene in a host cell. For example, it includes a plasmid vector, a cosmid vector, and a virus vector such as a bacteriophage vector, an adenovirus vector, a retrovirus vector and an adeno-associated virus vector. Suitable recombinant vectors may be constructed by manipulating plasmids often used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, and the like), a phage (for example, $\lambda gt4\lambda B$, $\lambda$-Charon, $\lambda\Delta z1$, M13, and the like), or a virus (for example, SV40, and the like), but not be limited thereto.

In the recombinant vector, the polynucleotides may be operatively linked to a promoter. The term "operatively linked" used herein refers to a functional linkage between a nucleotide expression regulating sequence (for example, a promoter sequence) and other nucleotide sequences. Thus, the regulating sequence may regulate the transcription and/or translation of the other nucleotide sequences by being operatively linked.

The recombinant vector may be constructed for cloning or expression. The expression vector may be any ordinary vectors known in the pertinent art for expressing an exogenous protein in plants, animals, or microorganisms. The recombinant vector may be constructed using various methods known in the art.

The recombinant vector may be constructed using a prokaryotic cell or a eukaryotic cell as a host. For example, when a prokaryotic cell is used as a host cell, the expression vector used generally includes a strong promoter capable of initiating transcription (for example, $pL^\lambda$ promoter, CMV promoter, trp promoter, lac promoter, tac promoter, T7 promoter, and the like), a ribosome binding site for initiating translation, and a transcription/translation termination sequence. When a eukaryotic cell is used as a host cell, the vector used generally includes the origin of replication acting in the eukaryotic cell, for example, an f1 replication origin, a SV40 replication origin, a pMB1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter, and the like) or a promoter derived from mammalian viruses (for example, an adenovirus late promoter, a vaccinia virus 7.5K promoter, a SV40 promoter, a cytomegalovirus promoter, a tk promoter of HSV, and the like). A transcription termination sequence in an expression vector for a eukaryotic host cell may be, in general, a polyadenylation sequence.

The recombinant cell may be those obtained by transfecting the recombinant vector into a suitable host cell. Any host cells known in the pertinent art to enable stable and continuous cloning or expression of the recombinant vector may be used as the hose cell. Suitable prokaryotic host cells may be one or more selected from E. coli JM109, E. coli BL21, E. coli RR1, E. coli LE392, E. coli B, E. coli X 1776, E. coli W3110, Bacillus species strains such as Bacillus subtillis, or Bacillus thuringiensis, intestinal bacteria and strains such as Salmonella typhymurum, Serratia marcescens, and various Pseudomonas species. Suitable eukaryotic host cells to be transformed may be one or more selected from yeasts, such as Saccharomyces cerevisiae, insect cells, plant cells, and animal cells, for example, Sp2/0, Chinese hamster ovary (CHO) K1, CHO DG44, PER.C6, W138, BHK, COS-7, 293, HepG2, Huh7, 3T3, RIN, and MDCK cell lines, but not be limited thereto.

The polynucleotide or the recombinant vector including the same may be transferred (transfected) into a host cell by using known transfer methods. Suitable transfer methods for prokaryotic host cells may include a method using $CaCl_2$ and electroporation. Suitable transfer methods for eukaryotic host cells may include microinjection, calcium phosphate precipitation, electroporation, liposome-mediated transfection, and gene bombardment, but are not limited thereto.

A transformed host cell may be selected using a phenotype expressed by a selected marker by any methods known in the art. For example, if the selected marker is a gene that is resistant to a specific antibiotic, a transformant may be easily selected by being cultured in a medium including the antibiotic.

The anti-c-Met/anti-EGFR bispecific antibody may be expected to exhibit an improved effect compared to a previously known anti-c-Met antibody, as follows:

1. an increased cancer cell inhibition effect compared to pre-existing anti-c-Met antibodies or EGFR-targeting drugs.

2. a cancer cell inhibition effect on a cancer cells having resistance to pre-existing anti-c-Met antibodies or EGFR-targeting drugs.

Hereafter, the present invention will be described in detail by examples.

The following examples are intended merely to illustrate the invention and are not construed to restrict the invention.

EXAMPLES

Reference Example 1

Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1-2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of 5×10$^5$ cells/ml, and after 24 hours, when the cell number reached to 1×10$^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA: light chain DNA) and mixed with 2 ml of OptiPro™ SFM (Invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of 5×10$^5$ cells/ml, and after 24 hours, when the cell number reached to 1×10$^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA: light chain DNA) and mixed with 2 ml of OptiPro™ SFM (invtrogen)

(A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFv Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker including the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 2, below.

TABLE 2

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 3 and were converted into IgG forms. Four antibodies which were respectively produced from clones L3-1, L3-2, L3-3, and L3-5 were used in the subsequent experiments.

TABLE 3

| Clone | Library onstructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI—CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA: light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. The histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was selected for the following examples, and name as L3-1Y-IgG2.

Example 1

Preparation of Anti-EGFR scFv

An anti-EGFR scFv binding to EGFR was prepared by inserting a peptide linker of (GGGGS)$_3$ between a heavy chain variable region of SEQ ID NO: 115 and a light chain variable region of SEQ ID NO: 116. In particular, the DNA sequence encoding a (GGGGS)$_3$ linker peptide was added to the DNA sequence (SEQ ID NO: 119) encoding the heavy chain variable region (SEQ ID NO: 115) and the DNA sequence (SEQ ID NO: 120) encoding the light chain variable region (SEQ ID NO: 116) of a humanized anti-EGFR antibody using an automatic gene synthesis (Bioneer Inc.) to synthesize a DNA fragment encoding a scFv of the anti-EGFR antibody. An anti-EGFR scFv prepared from the synthesized DNA fragment was named as "anti-EGFR antibody E-2".

The amino acid sequences of the heavy chain variable region and the light chain variable region of the prepared anti-EGFR scFv, and coding nucleotide sequences thereof are summarized in Table 4, as follows (wherein the sequences marked in bold type indicate CDRs, i.e., CDR-H1, CDR-H2, and CDR-H3, or CDR-L1, CDR-L2, and CDR-L3, in sequence):

TABLE 4

|  | Heavy chain variable region of anti-EGFR antibody E-2 | Light chain variable region of anti-EGFR antibody E-2 |
| --- | --- | --- |
| Amino acid sequence | EVQLLESGGGLVQPGGSLRL SCAASGFTFSNYDMSWVRQ APGKGLEWVSGISHSSGSKY YADSVKGRFTISRDNSKNTL YLQMNSLRAEDTAVYYCAK DATPRPLKPFDYWGQGTLV TVSS (SEQ ID NO: 115) | QSVLTQPPSASGTPGQRVTISC TGSSSNIGNNDVSWYQQLPG TAPKLLIYDDNKRPSGVPDRF SGSKSGTSASLAISGLRSEDEA DYYCGSWDASLNAYVFGGG TKLTVLG (SEQ ID NO: 116) |
| Coding nucleotide sequence | GAGGTGCAGCTGTTGGAGT CTGGGGGAGGCTTGGTACA GCCTGGGGGGTCCCTGAGA CTCTCCTGTGCAGCCTCTGG ATTCACCTTTAGCAATTAT GATATGAGCTGGGTCCGCC AGGCTCCAGGGAAGGGGCT GGAGTGGGTCTCAGGGAT CTCTCATAGTAGTGGTAG TAAATATTACGCTGATTC TGTAAAAGGTCGGTTCACC ATCTCCAGAGACAATTCCA AGAACACGCTGTATCTGCA AATGAACAGCCTGAGAGCC GAGGACACGGCCGTGTATT ACTGTGCGAAAGATGCTA CTCCGCGTCCGCTGAAGC CTTTCGACTACTGGGGCCA GGGTACACTGGTCACCGTG AGCTCA (SEQ ID NO: 119) | CAGTCTGTGCTGACTCAGCC ACCCTCAGCGTCTGGGACCC CCGGGCAGAGGGTCACCATC TCTTGTACTGGCTCTTCATC TAATATTGGCAATAATGAT GTCTCCTGGTACCAGCAGCT CCCAGGAACGGCCCCCAAAC TCCTCATCTATGATGATAAT AAGCGGCCAAGCGGGGTCC CTGACCGATTCTCTGGCTCC AAATCTGGCACCTCAGCCTC CCTGGCCATCAGTGGGCTCC GGTCCGAGGATGAGGCTGAT TATTACTGTGGTTCTTGGGA TGCTAGCCTGAATGCTTAT GTCTTCGGCGGAGGCACCAA GCTGACGGTCCTAGGC (SEQ ID NO: 120) |

A modified anti-EGFR scFv (heavy chain variable region: SEQ ID NO: 117 and light chain variable region: SEQ ID NO: 118) was prepared as described above, with the exception that the amino acid, G, at 44$^{th}$ position of the heavy chain variable region (SEQ ID NO: 115) was substituted with C, and the amino acid, G, at 100$^{th}$ position of the light chain variable region (SEQ ID NO: 116) was substituted with C. The amino acid location within the antibody complies with kabat numbering system. Such modifications (substitutions) can increase the stability of the anti-EGFR scFv.

<SEQ ID NO: 117: heavy chain variable region of modified anti-EGFR antibody E-2>

EVQLLESGGGLVQPGGSLRLSCAASGFTFSNYDMSWVRQAPGKCLEWV

SGISHSSGSKYYADSVKGRFTISRDNSKNTLYLQMNSLRAEDTAVYYC

AKDATPRPLKPFDYWGQGTLVTVSS (wherein the sequences marked in bold type indicate CDRs, i.e., CDR-H1, CDR-H2, and CDR-H3, in sequence)

<SEQ ID NO: 118: light chain variable region of modified anti-EGFR antibody E-2>

QSVLTQPPSASGTPGQRVTISCTGSSSNIGNNDVSWYQQLPGTAPKLLIY

DDNKRPSGVPDRFSGSKSGTSASLAISGLRSEDEADYYCGSWDASLNAYV

FGCGTKLTVLG (wherein the sequences marked in bold type indicate CDRs, i.e., CDR-L1, CDR-L2, and CDR-L3, in sequence)

The thus obtained modified anti-EGFR scFv (including SEQ ID NO: 117 and SEQ ID NO: 118) was used to manufacture the following bispecific antibodies.

Example 2

Preparation of Anti-c-Met/Anti-EGFR Bispecific Antibody

The modified anti-EGFR scFv (including SEQ ID NO: 117 and SEQ ID NO: 118) prepared in the above Example 1 was fused at the c-terminal of Fc of the anti-c-Met antibody L3-1Y-IgG2 prepared in the above reference example 1. The fusion procedures are as follows.

A DNA segment having a base sequence (SEQ ID NO: 66) corresponding to the heavy chain of the anti-c-Met antibody L3-1Y-IgG2 prepared in above reference example 1 was inserted into a pcDNA™3.3-TOPO TA Cloning Kit (Cat no. 8300-01) which is included in OptiCHO™ Antibody Express Kit (Cat no. 12762-019) by Invitrogen Inc., and a DNA segment having a base sequence (SEQ ID NO: 68) corresponding to the light chain of the anti-c-Met antibody L3-1Y-IgG2 was inserted into a pOptiVEC™-TOPO TA Cloning Kit. Thereafter, the anti-EGFR scFv coding DNA prepared in Example 1 was fused at the c-terminal of Fc of L3-1Y-IgG2 inserted into pcDNA™3.3, using the coding DNA sequence of a linker peptide having 10 amino acid lengths consisting of (G4S)2, to construct vectors for the expression of bispecific antibodies.

The constructed vectors were each amplified using Qiagen Maxiprep kit (Cat no. 12662 and their temporary expressions were performed using Freestyle™ MAX 293 Expression System (invitrogen). A cell line used was 293 F cells, which were cultured in a suspension culture manner using FreeStyle™ 293 Expression Medium as a medium. One day before the temporary expression, the cells were prepared at a concentration of $5 \times 10^5$ cells/ml and after 24 hours, their temporary expression started when the number of the cells reached $1 \times 10^6$ cells/ml. Transfection was performed by a liposomal reagent method using Freestyle™ MAX reagent (Invitrogen). DNA was prepared in a 15-ml tube in a ratio of heavy chain DNA:light chain DNA=3:2 and mixed with 2 ml of OptiPro™ SFM (invtrogen) (A), and 100 μl of Freestyle™ MAX reagent and 2 ml of OptiPro™ SFM were mixed in another 15-ml tube (B), and after (A) and (B) were mixed and incubated for 15 min., the mixture solution was then slowly mixed into the cells which were prepared one day before. After the transfection was complete, the cells were cultured in a 37° C., 80% humidity, 8% $CO_2$, 130 rpm incubator for 5 days.

The cultured cells were centrifuged to obtain each 100 ml of supernatants, which were then purified using AKTA Prime (GE healthcare). The culture was flowed at a flow rate of 5 ml/min. onto the AKTA Prime installed with Protein A column (GE healthcare, 17-0405-03) to perform elution using an IgG elution buffer (Thermo Scientific, 21004). The buffer was replaced by a PBS buffer to finally obtain purified bispecific anti-c-Met/anti-EGFR antibodies.

The thus prepared anti-c-Met/anti-EGFR bispecific antibody in which the modified anti-EGFR scFv is fused at the c-terminal of L3-1Y-IgG2 was named ME22S.

Example 3

Properties of Anti-c-Met/Anti-EGFR Bispecific Antibody

To examine the property of the anti-c-Met/anti-EGFR bispecific antibody ME22S prepared in Example 2, 20 ug of ME22S was injected into HPLC system (WATERS 2695) equipped with TSKG3000SWXL column (Tosho) at the velocity of 0.5 ml/min, to conduct Size Exclusion Chromatography by HPLC.

Figure 2:
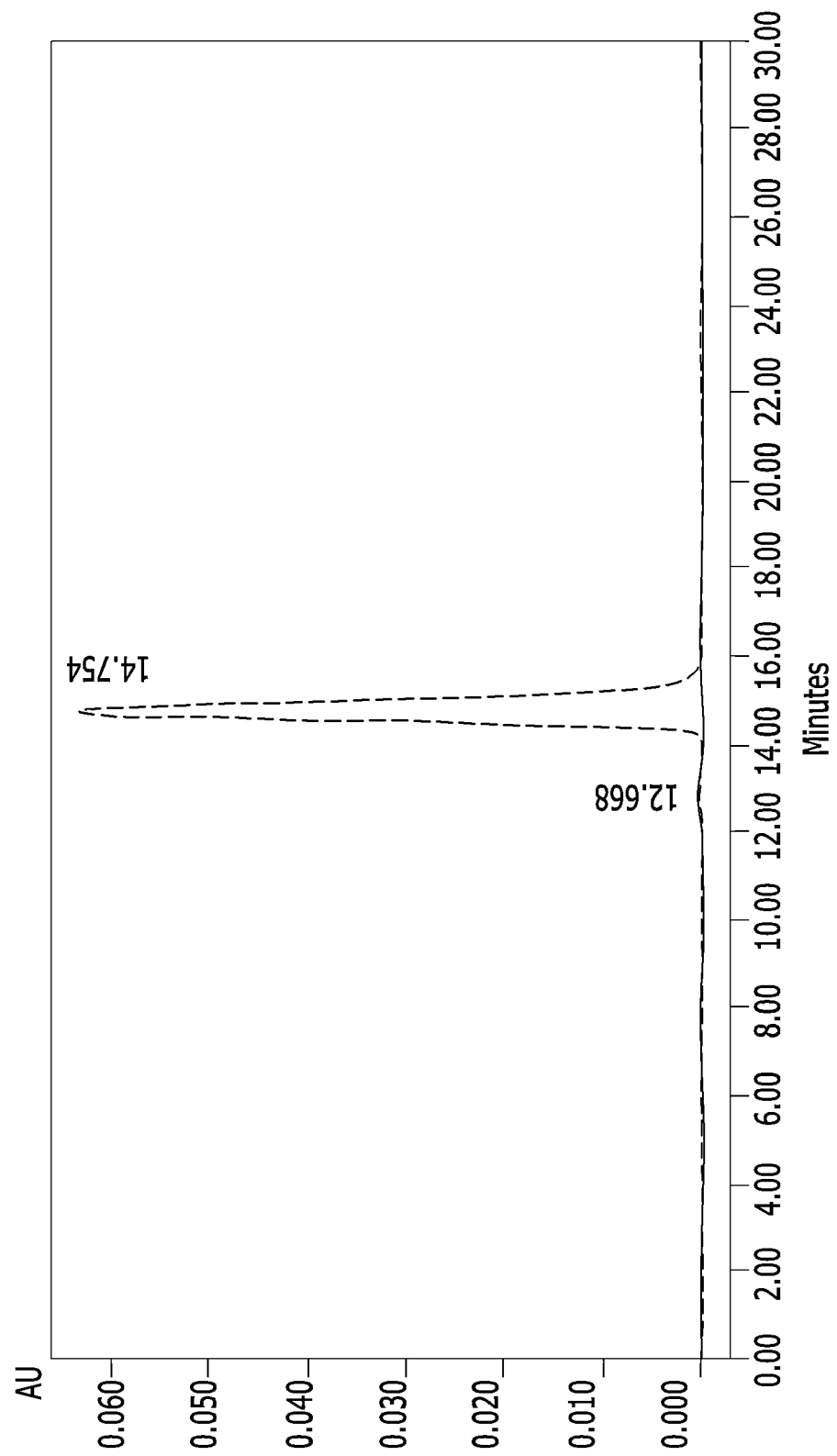
FIG. 2 is a size exclusion chromatography displaying a monomeric property of the purified anti-c-Met/anti-EGFR bispecific antibody according to an embodiment.

The obtained results are shown in FIG. 2. As shown in FIG. 2, the anti-c-Met/anti-EGFR bispecific antibody ME22S forms a slight amount of soluble dimer (<1%)m, indicating that it is very stable molecule.

Example 4

Dual Binding of Anti-c-Met/Anti-EGFR Bispecific Antibody

To examine whether the anti-c-Met/anti-EGFR bispecific antibody recognizes both of the antigens, c-Met and EGFR, the experimentation using Biacore T100 (GE) was performed. An anti-6xHis antibody (#MAB050, R&D Systems) was immobilized onto a CM5 chip (#BR-1005-30, GE) using an amine coupling kit (#BR-1000-50, GE) according to the manufacturer's instructions. After the immobilization, c-Met-Fc (#358-MT/CF, R&D Systems) was injected thereto at the amount of 15 μg/m for 1 min. Then, the bispecific antibody ME22S prepared in Example 2 was injected at the amount of 20 nM for 1 min. Thereafter, EGFR-Fc (#344-ER, R&D Systems) was injected at 100 nM for 1 min and then, association/dissociation was observed.

In addition, the affinities of the prepared anti-c-Met/anti-EGFR bispecific antibody to the two types of antigens, c-Met and EGFR, were each identified using Biacore T100 (GE). A human Fab binder (GE Healthcare) was immobilized at the surface of a CM5 chip (#BR-1005-30, GE) according to the manufacturer's specifications. About 90 to 120 Ru of ME22S was captured, and c-Met-Fc (#358-MT/CF, R&D Systems) or EGFR-Fc (#344-ER, R&D Systems) were injected at various concentrations into the captured antibody. 10 mM Glycine-HCl (pH 1.5) solution was injected thereto to regenerate the surface. In order to measure affinity, the data obtained from this experiment was fitted using BIAevaluation software (GE Healthcare, Biacore T100 evaluation software).

Figure 3:
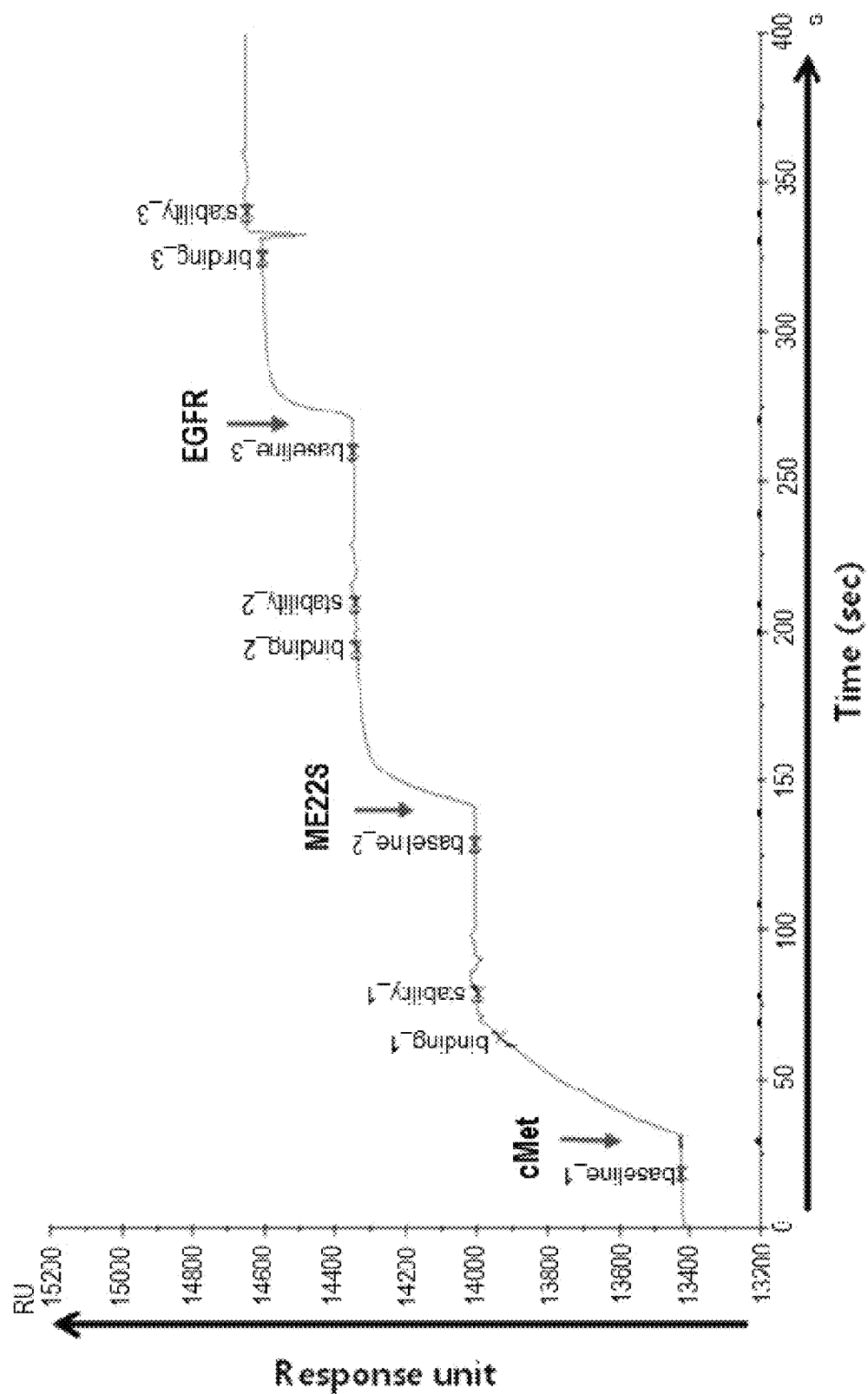
FIG. 3 is a graph displaying the binding affinities to EGFR and c-Met of an anti-c-Met/anti-EGFR bispecific antibody according to an embodiment.
Figure 4A:
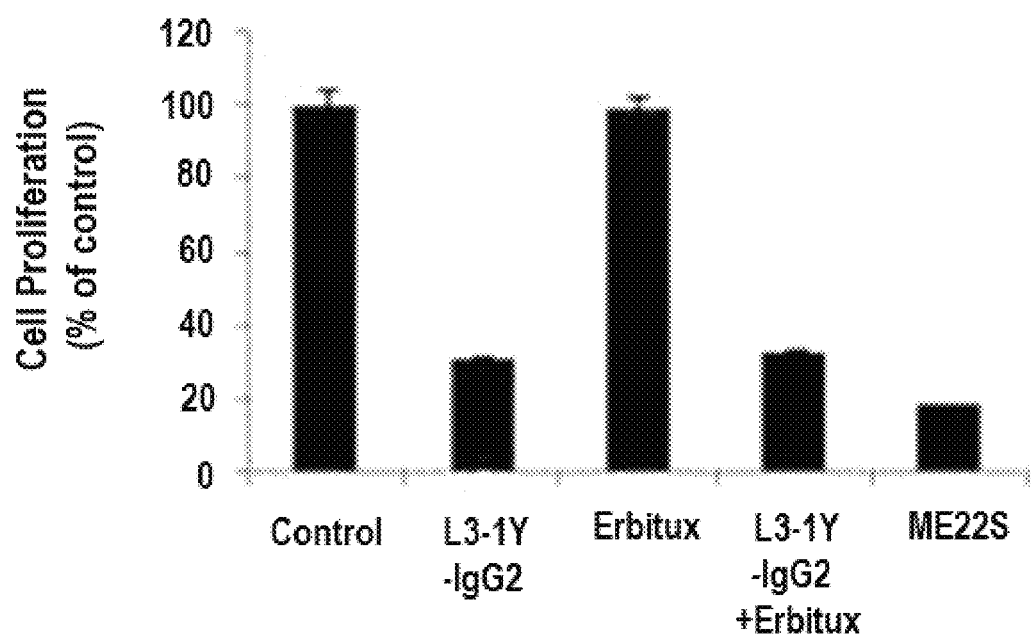
FIG. 4A is a graph displaying the cell growth of various cancer cells treated with antibodies including an anti-c-Met/anti-EGFR bispecific antibody according to an embodiment, which is calculated as a relative value to that of a control (media, without antibody).
Figure 4B:
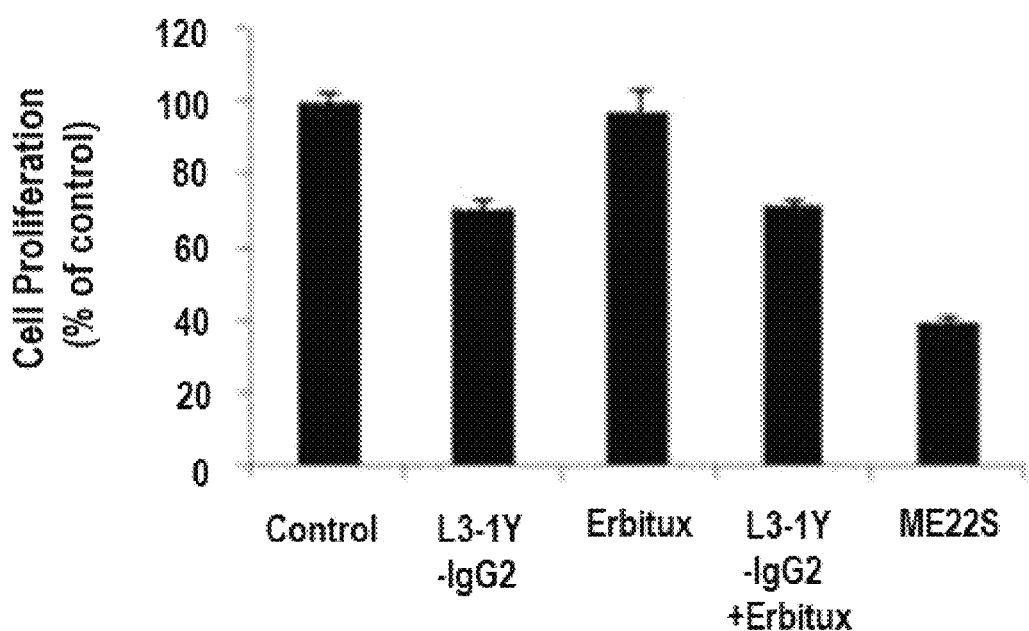
FIG. 4B is a graph displaying the cell growth of various cancer cells treated with antibodies including an anti-c-Met/anti-EGFR bispecific antibody according to an embodiment, which is calculated as a relative value to that of a control (media, without antibody).
Figure 4C:
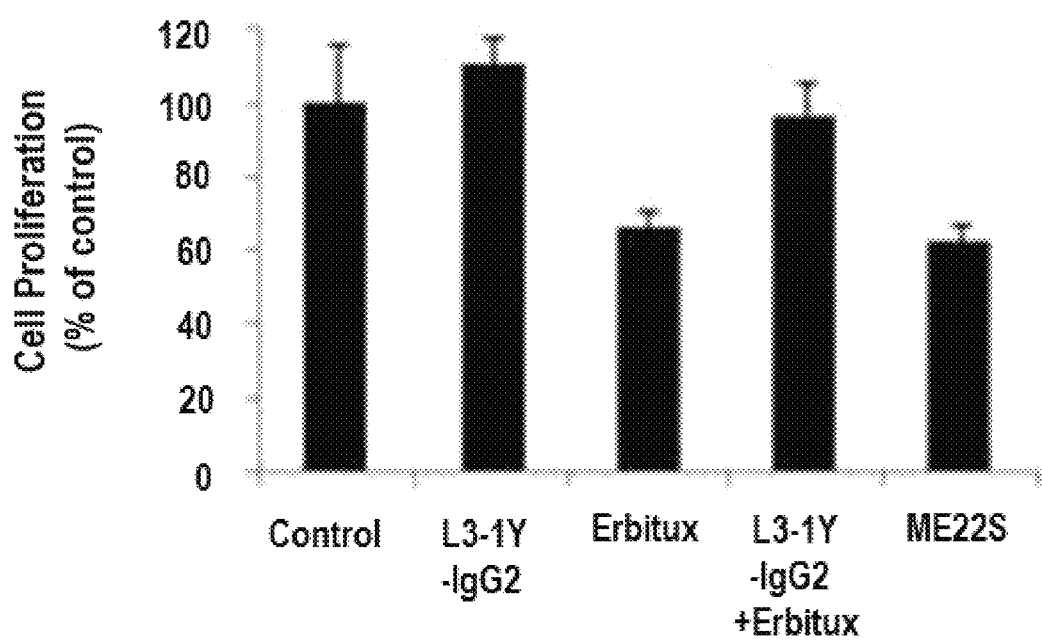
FIG. 4C is a graph displaying the cell growth of various cancer cells treated with antibodies including an anti-c-Met/anti-EGFR bispecific antibody according to an embodiment, which is calculated as a relative value to that of a control (media, without antibody).
Figure 4D:
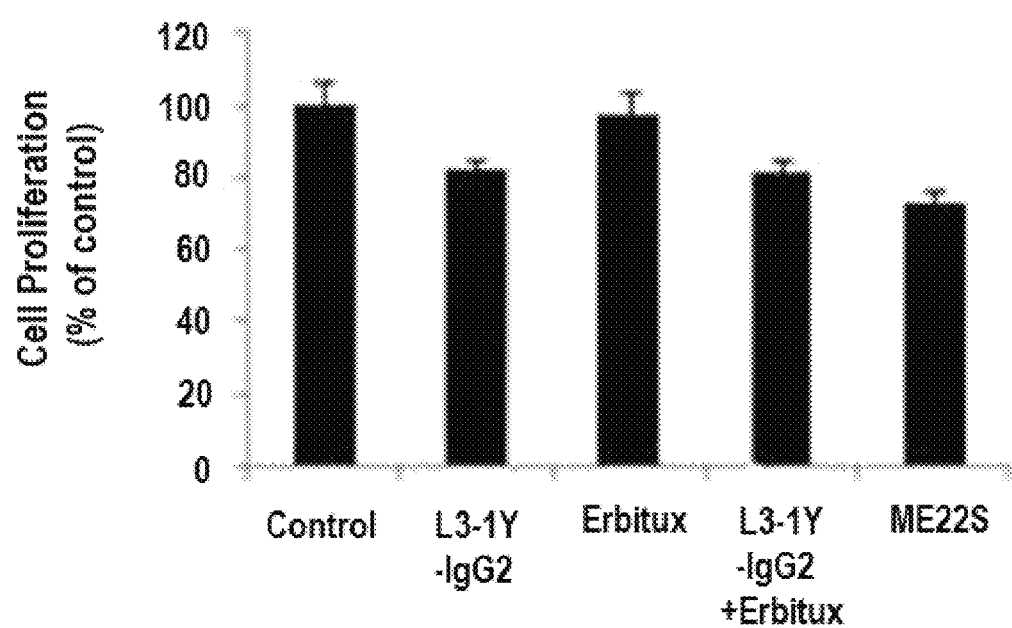
FIG. 4D is a graph displaying the cell growth of various cancer cells treated with antibodies including an anti-c-Met/anti-EGFR bispecific antibody according to an embodiment, which is calculated as a relative value to that of a control (media, without antibody).
Figure 4E:
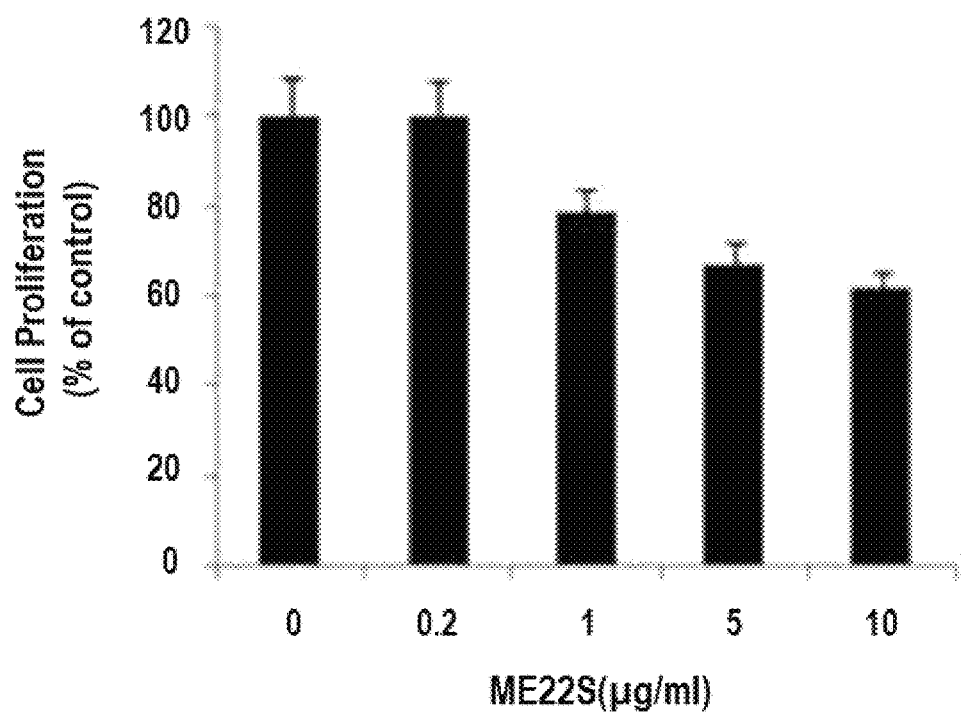
FIG. 4E is a graph displaying the cell growth of various cancer cells treated with antibodies including an anti-c-Met/anti-EGFR bispecific antibody according to an embodiment, which is calculated as a relative value to that of a control (media, without antibody).
Figure 4F:
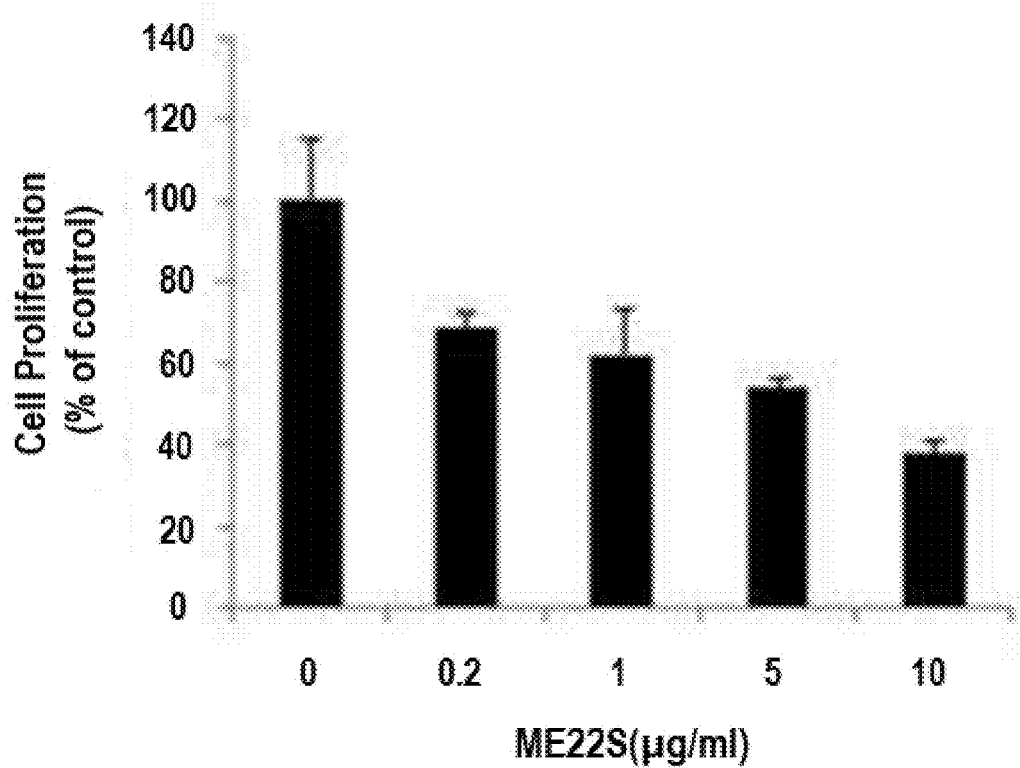
FIG. 4F is a graph displaying the cell growth of various cancer cells treated with antibodies including an anti-c-Met/anti-EGFR bispecific antibody according to an embodiment, which is calculated as a relative value to that of a control (media, without antibody).

The obtained results are shown in Table 5 and FIG. 3, wherein it is confirmed that ME22S binds to both of the two antigens, c-Met and EGFR.

TABLE 5

| Antibody | Antigen | $K_D$ (nM) | $k_a$ (1/Ms) | $k_d$ (1/s) |
|---|---|---|---|---|
| ME22S | cMet | 0.05 | $1.3 \times 10^5$ | $5.5 \times 10^{-5}$ |
|  | EGFR | 0.49 | $1.9 \times 10^5$ | $9.2 \times 10^{-5}$ |

Example 5

Examination of Cancer Cell Proliferation Inhibition by Anti-c-Met/Anti-EGFR Bispecific Antibody The cancer cell proliferation inhibition effects of the anti-c-Met/anti-EGFR bispecific antibody prepared in Example 2 were examined in stomach cancer cell lines SNU5 and SNU638, human skin cancer cell line A431, human lung cancer cell line NCI-H1993, and human head and neck cancer cell lines HN3 and K2D. SNU5, SNU638, A431, NCI-H1993, and HN3 cell lines were all purchased from ATCC. K2D cell line, which is a patient derived cell line, was donated from Medical College of Konkuk University.

A1 cells except A431 were incubated in RPMI1640 medium (#11875-093, Gibco) supplemented with 10% (v/v) FBS and 1% (v/v) Penicillin-Streptomycin under the conditions of 5% $CO_2$ and 37° C. A431 cells were incubated in DMEM medium (#30-2002, ATCC) supplemented with 10%

(v/v) FBS and 1% (v/v) Penicillin-Streptomycin under the conditions of 5% $CO_2$ and 37° C. For cell proliferation assay, each cell line was sub-cultured at a concentration of $5×10^3$ cell/well in a 96-well plate, which was treated with the anti-c-Met/anti-EGFR bispecific antibody ME22S prepared in Example 2 in an amount of 0.25 ug (microgram)/ml (SNU5 cell line) or 5 µg/m (SNU638, A431, and NCI-H1993 cell lines), and cultured for 72 hours. A medium with no antibody was used as a negative control, and commercially available EGFR inhibitor Erbitux® (#ET509081213, Merck) treated group, L3-1Y-IgG2 antibody (prepared in reference example) treated group, and co-treated group of L3-1Y-IgG2 and Erbitux® were each used as positive controls. The amount of Erbitux® and L3-1Y-IgG2 were 0.25 µg/ml for SNU5 and 5 µg/m for SNU638, A431, and NCI-H1993 cell lines. HN3 and K2D cell lines were treated with ME22S by serially diluting from 10 µg/ml to 5-fold dilution concentration and incubated for 72 hours.

After incubation, cell proliferation degrees were analyzed using Cell Counting Kit-8 assay (Dojindo Molecular Technologies, Gaithersburg, Md.) according to the manufacturer's instructions. In brief, after the incubation for 72 hours, 10 µl (microliter) of CCK8 solution was added to each well and after the additional incubation for 2.5 hours, absorption degrees were read at 450 nm using a microplate reader.

The obtained results are shown in FIGS. 4A to 4F. As seen in FIGS. 4A to 4F, the anti-c-Met/anti-EGFR bispecific antibody ME22S showed remarkable increases in cell proliferation inhibitory effects, compared to the cases treated individually with the anti-c-Met antibody L3-1Y-IgG2 and the anti-EGFR antibody Erbitux®. In particular, the anti-c-Met/anti-EGFR bispecific antibody ME22S showed excellent cell proliferation inhibitory effects, even compared to the co-treatment case (L3-1Y-IgG2+Erbitux®), which is not a form of bispecific antibody.

Example 6

Examination of Cancer Cell Proliferation Inhibition by Anti-c-Met/Anti-EGFR Bispecific Antibody in Resistance-Induced Cancer Cells Cell lines N87(ATCC) and NCI-H820(ATCC) were incubated in RPMI1640 medium supplemented with 10% (v/v) FBS and 1% (v/v) Penicillin-Streptomycin under the condition of 5% $CO_2$ and 37° C. For cell proliferation assay, N87 cell line was sub-cultured at a concentration of $5×10^3$ cell/well in a 96-well plate, which was treated with 500 nM of Lapatinib (sc-353686, Santa Cruz Biotechnology) alone, 500 nM of Lapatinib and 1 µg/m of L3-1Y-IgG2 (co-treatment), 500 nM of Lapatinib and 1 µg/m of Erbitux® (co-treatment), and 500 nM of Lapatinib and 1 µg/m of ME-22S (co-treatment), and cultured for 72 hours. For resistance induction, 100 ng/ml of HGF (PGR 101-200, Pangen) was added to each of the above treatment groups and cultured for 72 hours together.

NCI-H820 cell line was sub-cultured at a concentration of $5×10^3$ cell/well in a 96-well plate, which was treated with 5 µg/m of ME-22S, and cultured for 72 hours. A medium with no antibody was used as a negative control, and commercially available EGFR inhibitor Erbitux® (#ET509081213, Merck) treated group, L3-1Y-IgG2 antibody (prepared in reference example) treated group, and co-treated group of L3-1Y-IgG2 and Erbitux® were each used as positive controls. The amount of each of Erbitux® and L3-1Y-IgG2 was 5 µg/m for each group. For resistance induction, 100 ng/ml of HGF (PGR 101-200, Pangen) was added to each of the above treatment groups and cultured for 72 hours together.

After incubation, cell proliferation degrees were analyzed using Cell Counting Kit-8 assay (Dojindo Molecular Technologies, Gaithersburg, Md.) according to the manufacturer's instructions. In brief, after the incubation for 72 hours, 10 µl of CCK8 solution was added to each well and after the additional incubation for 2.5 hours, absorption degrees were read at 450 nm using a microplate reader.

The obtained results are shown in FIG. 5. As seen in FIG. 5, the anti-c-Met/anti-EGFR bispecific antibody ME22S showed remarkable increases in cell proliferation inhibitory effects on N87 and H820 cell lines where a resistance is induced by HGF treatment as well as N87 and H820 cell lines treated with no HGF.

Example 7

C-Met and EGFR Activation Inhibitory Effect of Anti-c-Met/Anti-EGFR Bispecific Antibody SNU638 cells were treated with Erbitux®, L3-1Y-IgG2 (Reference Example 1) and ME22S (Example 2), alone or in combination, for 40 minutes. Then each of HGF and EGF (236-EG-200, R&D systems) was added thereto at the amount of 100 ng/ml. Then, the cells were lysed with Complete Lysis-M (#04719956001, Roche), and the resulted cell lysates were collected and subject to SDS-PAGE electrophoresis.

After the electrophoresis, the proteins from the gels were transferred onto a nitrocellulose membrane (#LC2006, Invitrogen), which was then blocked with a skim milk (5% in TBST) at a room temperature for one hour. After blocking, for the primary antibody reaction, the membrane was treated with a 1:1000 dilution of anti-phospho c-Met antibody, anti-phospho EGFR antibody, anti-EGFR antibody, anti-phosphor Akt antibody, anti-Akt antibody (all available from Cell signaling technology), and anti-c-Met antibody (Abcam) in an amount of 10 µg/ml at a room temperature for two hours. After the primary antibody reaction, the membrane was washed three times with PBS for 5 min. and then, it was treated with a horseradish peroxidase attached secondary antibody (Cell signaling technology) against each primary antibody in an amount of 1 µg/ml at a room temperature for one hour. After the secondary antibody reaction, the membrane was washed three times with PBS for 5 min. and then sensitized with Enhanced chemiluminescence substrate (Thermo scientific) to measure the degree of antigen-antibody reaction by ImageQuant LAS system (GE Healthcare).

Figure 6:
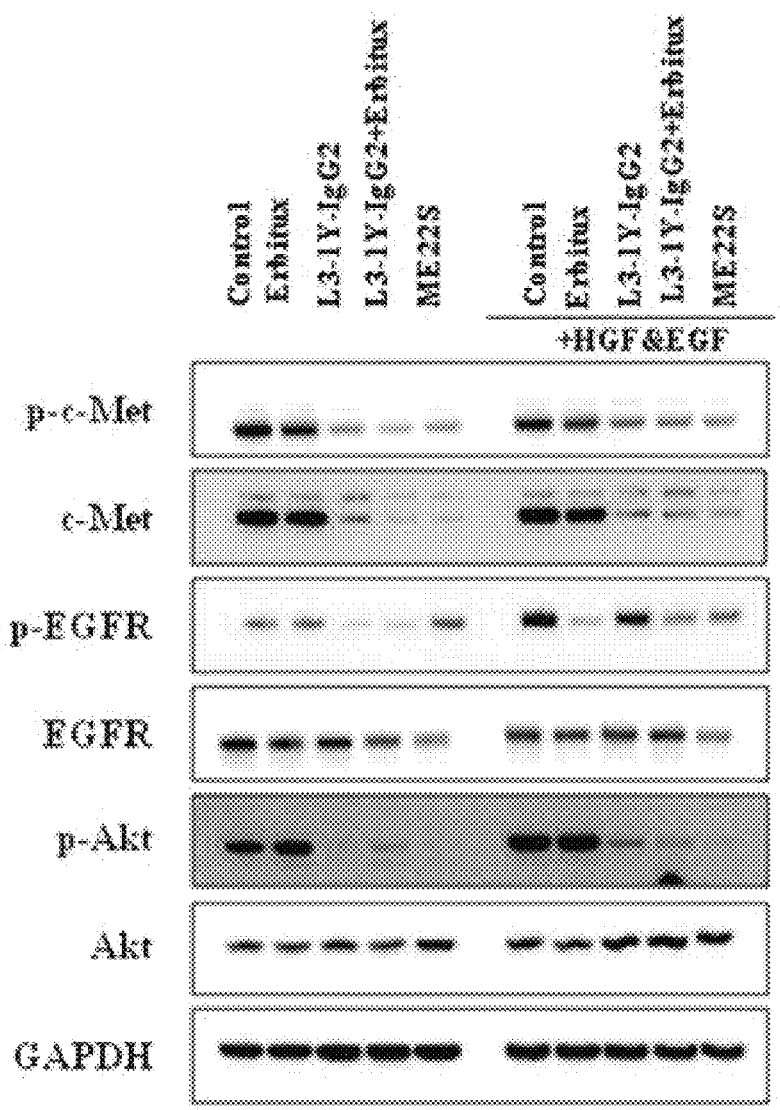
FIG. 6 is an immunoblot showing the phosphorylation and degradation of c-Met and EGFR when treated with antibodies including an anti-c-Met/anti-EGFR bispecific antibody according to an embodiment.

The obtained results are shown in FIG. 6. As shown in FIG. 6, the treatment of the anti-c-Met/anti-EGFR bispecific antibody ME22S results in increased c-Met phosphorylation inhibition and c-Met degradation, compared with treatment of anti-c-Met antibody L3-1Y-IgG2 alone, and L3-1Y-IgG2 and EGFR inhibitor Erbitux® in combination. In addition, when EGFR inhibitor Erbitux® is treated alone or in combination with L3-1Y-IgG2, EGFR phosphorylation inhibition is observed, but EGFR degradation is nearly not observed. When the anti-c-Met/anti-EGFR bispecific antibody ME22S is treated, EGFR degradation as well as EGFR phosphorylation inhibition is observed. Such results indicate that the anti-c-Met/anti-EGFR bispecific antibody ME22S has EGFR degradation activity as well as EGFR phosphorylation inhibitory activity, indicating that an EGFR inhibitor such as anti-EGFR antibody can possess a synergistic effect by forming a bispecific antibody with an anti-c-Met antibody, compared to an EGFR inhibitor alone.

Example 8

Co-Localization of c-Met and EGFR by Anti-c-Met/Anti-EGFR Bispecific Antibody

SNU638 cells (ATCC) were provided at the amount of $4 \times 10^4$ cell/well, and treated with L3-1Y-IgG2 and anti-c-Met/anti-EGFR bispecific antibody ME22S alone or in combination at the amount of 5 µg/m per well (in the case of combination treatment, the amount of each antibody is 5 µg/m) under 37° C. for 4 hours. The cells were treated with 4% (v/v) formaldehyde for 15 minutes to be immobilized on a plate, and washed three times with PBS. Thereafter, the cells were treated with a blocking buffer (0.5% triton x-100 and 5% donkey serum) at a room temperature for one hour and then treated with a 1:100 dilution of primary antibodies against each of c-Met and EGFR (c-Met primary antibody; #FAB3582A, R&D systems, EGFR primary antibody; #5616, Cell signaling) against c-Met and EGFR, respectively in the amount of 100 µl, at 4° C. for 15 hours. After the cells were washed three time with PBS, they were treated with a 1:2000 dilution of a secondary antibody (#A21433, Invitrogen) in an amount of 100 ul at a room temperature for 1 hour and washed three times with PBS to prepare a plate with a mounting medium (#H-1200, Vector). The prepared cells were observed with a confocal microscope (Zeiss, LSM710).

Figure 7:
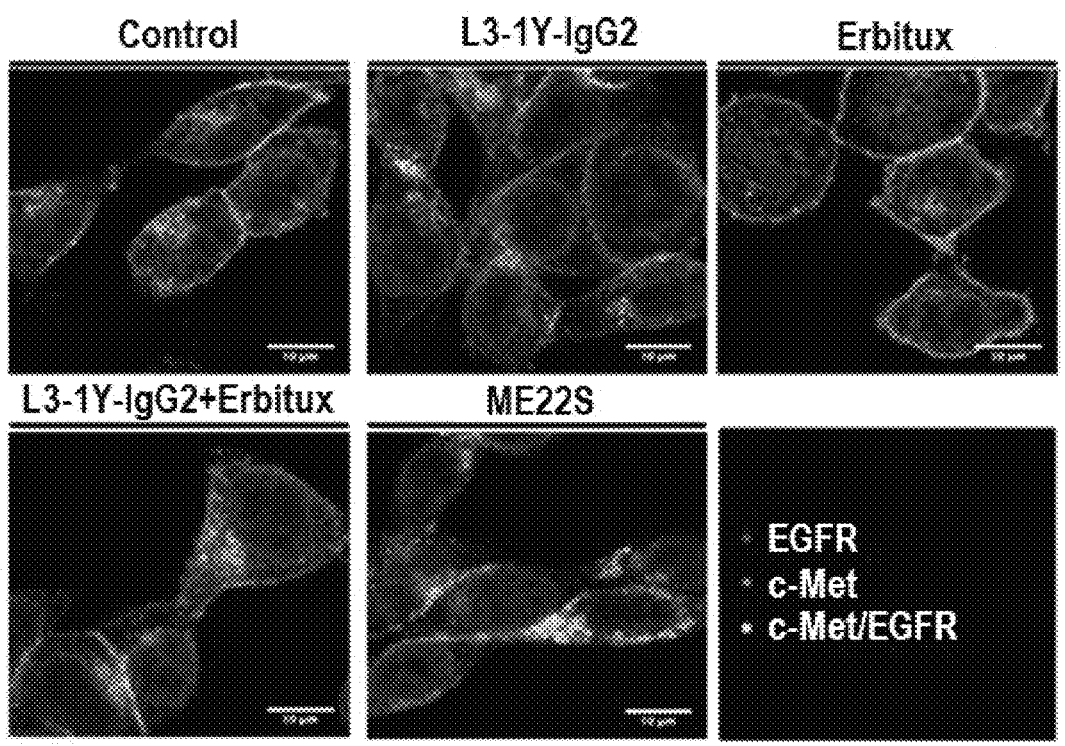
FIG. 7 provides fluorescence microscopic images of SNU638 gastric cancer cells showing co-localization of c-Met and EGFR after treating an anti-c-Met/anti-EGFR bispecific antibody according to an embodiment.

The obtained results are shown in FIG. 7. As seen in FIG. 7, when EGFR inhibitor Erbitux® is treated alone, EGFR locates on cell membranes, and even when L3-1Y-IgG2 and Erbitux® are treated together, c-Met migrates to inside of the cell but EGFR still locates on cell membrane. However, when the anti-c-Met/anti-EGFR bispecific antibody ME22S is treated, both of c-Met and EGFR migrate to inside of the cells.

Example 9

Decrease in Expression of Target Receptor by Anti-c-Met/Anti-EGFR Bispecific Antibody To examine decrease of expressed level of target receptors, c-Met and EGFR by ME22S, human stomach cancer cell line, MKN45 (ATCC) and SNU 638 (ATCC) were sub-cultured on 96-well plate, where the concentration of each cell line is $2 \times 10^3$ cell/well. The cells were treated with each of L3-1Y-IgG2, Erbitux®, and ME22S, at the amount of 5 µg/ml, and cultured for 24 hours. A medium with no antibody was used as a negative control. After culture, the cells were lysed with Complete Lysis-M (#04719956001, Roche), and cell lysates were collected. Total cMet detection ELISA kit (DYC358E, R&D systems) was used for measuring the expression level of c-Met, and Total EGF Receptor ELISA kit (#7297, Cell Signaling) for measuring the expression level of EGFR, according to manufacturer's indications.

Figure 8:
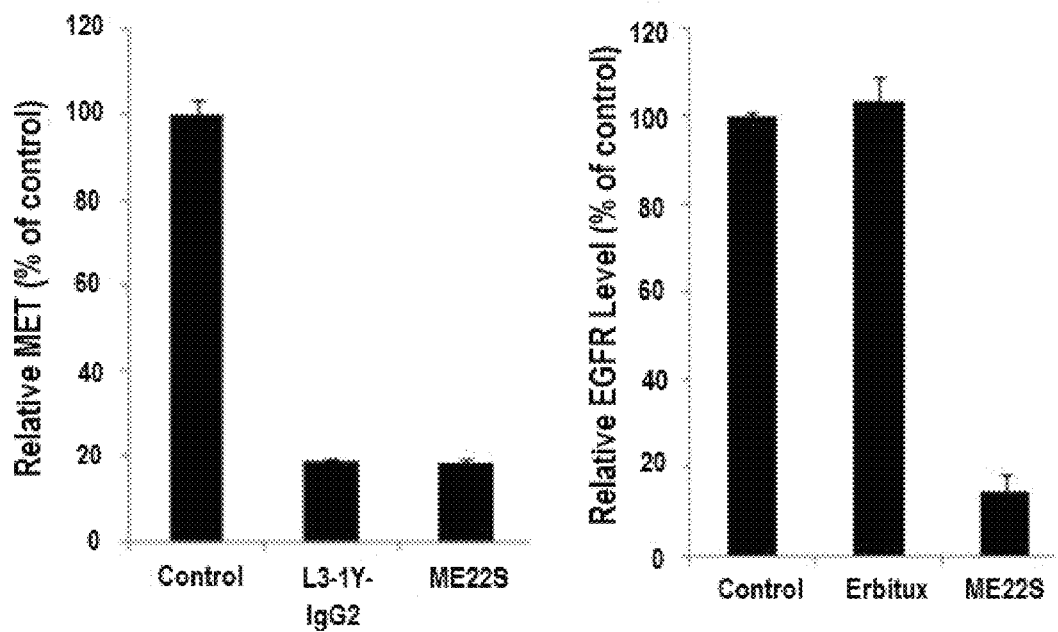
FIG. 8 consists of graphs displaying the expression levels of c-Met and EGFR when treated with an anti-c-Met antibody or with anti-c-Met/anti-EGFR bispecific antibody according to an embodiment, indicating the degradation of both of c-Met and EGFR by the anti-c-Met/anti-EGFR bispecific antibody.

The obtained results are shown in FIG. 8. As shown in FIG. 8, L3-1Y-IgG2 and ME22S considerably decrease the expression level of c-Met. Erbitux® does not effect on the expression level of EGFR, whereas ME22S considerably decreases the expression level of EGFR as well as the expression level of c-Met.

Example 10

Inhibition of Cancer Metastasis by Anti-c-Met/Anti-EGFR Bispecific Antibody

Human stomach cancer cell line, SNU638 cells (ATCC) were sub-cultured on trans-well CIM-16 plate (Roche Applied Bioscience) in the concentration of $1 \times 10^5$ cell/well. During the sub-culture, L3-1Y-IgG2, Erbitux®, and ME22S were treated alone or in combination, at the amount of 10 µg/ml, and to induce metastasis, HGF and EGF were treated at the amount of 100 ng/ml, respectively, simultaneously with the antibody treatment. The ratio of cancer metastasis was measured in real time using xCelligence RTCA DP instrument (Roche Applied Bioscience).

Figure 9:
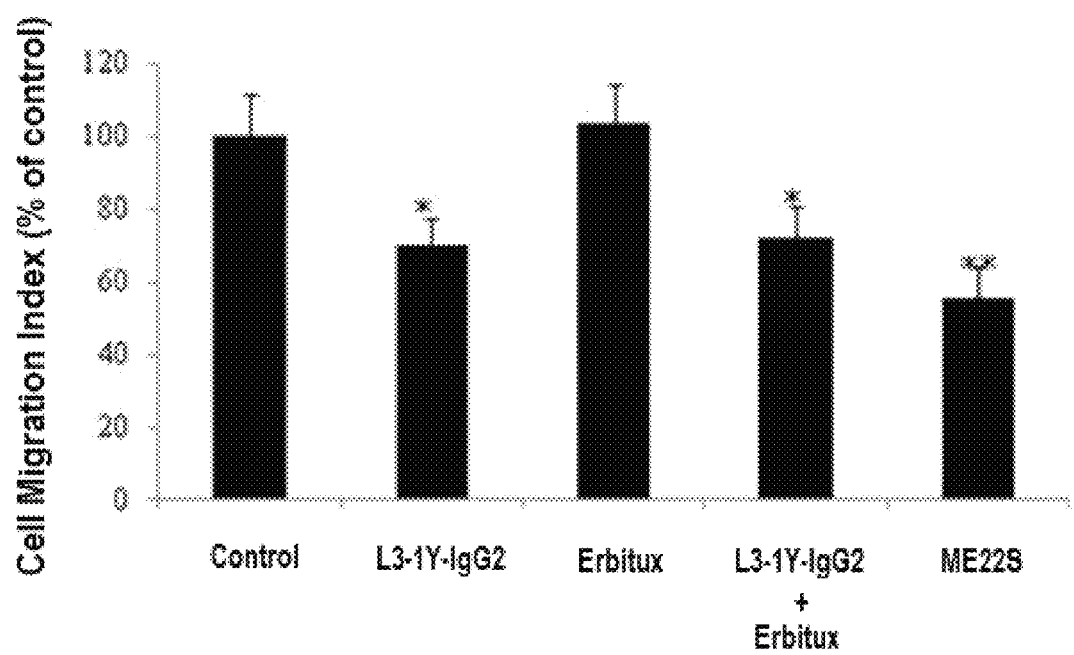
FIG. 9 consists of graphs displaying comparative cell migration level of SNU638 gastric cancer cells when treated with an anti-c-Met/anti-EGFR bispecific antibody according to an embodiment which is calculated as a relative value to that of a control (media, without antibody).

The obtained results are shown in FIG. 9. As shown in FIG. 9, the treatment of Erbitux® alone has no effect in inhibiting cancer metastasis, but the treatment L3-1Y-IgG2 alone and the combination treatment of L3-1Y-IgG2 and Erbitux® result in inhibiting cancer metastasis to the ratio of about 30%. However, ME22S exhibits more excellent inhibition ratio of cancer metastasis as about 45%, indicating that the anti-c-Met/anti-EGFR bispecific antibody is more effective in inhibition of cancer metastasis.

Example 11

Cancer Cell Inhibition Effect of Anti-c-Met/Anti-EGFR Bispecific Antibody

SNU5 cells (ATCC) were injected into dorsal subcutis of 5-6 week old CB.17-SCID mice (Shanghai SLAC Laboratory Animal Co. Ltd.) at the amount of $3 \times 10^6$ cell/mouse, to prepare tumor models. When the tumor volume reaches 100 mm³, 1 mg/kg of L3-1Y-IgG2 and 1 mg/kg of anti-c-Met/anti-EGFR bispecific antibody ME22S were intravenously administered alone or in combination once a week for 4 weeks in total. A group where PBS is intravenously administered thereto was used as a negative control, and a group where 10 mg/kg of an anticancer drug, Irinotecan (Pfizer Inc.), was intravenously administered thereto twice a week for 4 weeks in total, was used as a positive control. The tumor size (length×breadth×height) was measured twice each week, and at the last week, the mice were autopsied.

Figure 10:
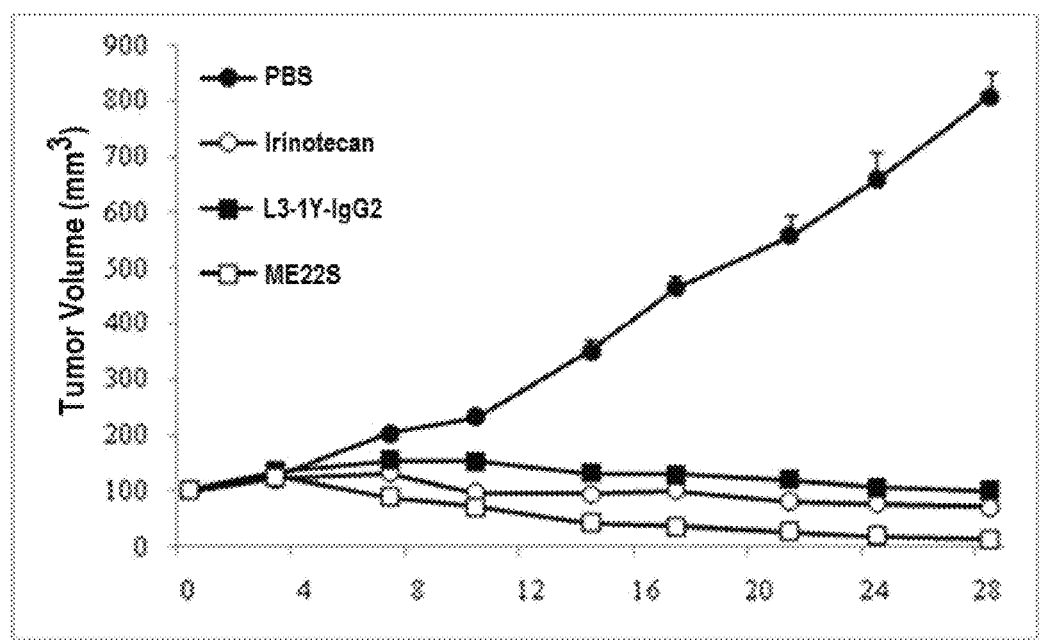
FIG. 10 is a graph displaying tumor volume change in a mouse xenograft model when treated with an anti-c-Met/anti-EGFR bispecific antibody according to an embodiment showing in vivo anti-tumor efficacy of bispecific antibody in animal cancer model.

The obtained tumor size is shown in FIG. 10. As shown in FIG. 10, when L3-1Y-IgG2 is treated alone, the tumor growth is inhibited and the final tumor size is nearly not increased from the initial size of 100 mm³, and the positive control shows the similar results where the final tumor size is about 72 mm³. However, when ME22S is treated, the tumor size becomes significantly decreased from 7 days after the administration, and the final tumor size is about 12 mm³. These results indicate that the anti-c-Met/anti-EGFR bispecific antibody has more increased inhibitory effect on cancer cell growth compared to L3-1Y-IgG2 and pre-existing drug, Irinotecan.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-EGFR antibody or an antigen-binding fragment thereof, comprising:
   a CDR-H1 comprising the amino acid sequence of SEQ ID NO: 109, a CDR-H2 comprising the amino acid sequence of SEQ ID NO: 110, a CDR-H3 comprising the amino acid sequence of SEQ ID NO: 111;
   a CDR-L1 comprising the amino acid sequence of SEQ ID NO: 112, a CDR-L2 comprising the amino acid sequence of SEQ ID NO: 113, and a CDR-L3 comprising the amino acid sequence of SEQ ID NO: 114.

2. The anti-EGFR antibody or an antigen-binding fragment thereof according to claim 1, comprising:
   a heavy chain variable region comprising the amino acid sequence of SEQ ID NO: 115 or SEQ ID NO: 117,
   a light chain variable region comprising the amino acid sequence of SEQ ID NO: 116 or SEQ ID NO: 118, or
   a combination thereof.

3. The anti-EGFR antibody or an antigen-binding fragment thereof according to claim 2, wherein the anti-EGFR antibody or an antigen-binding fragment is an anti-EGFR scFv comprising:
   a heavy chain variable region comprising the amino acid sequence of SEQ ID NO: 115 or SEQ ID NO: 117, and
   a light chain variable region comprising the amino acid sequence of SEQ ID NO: 116 or SEQ ID NO: 118.

4. An anti-c-Met/anti-EGFR bispecific antibody comprising an anti-c-Met antibody or an antigen-binding fragment thereof and an anti-EGFR antibody or an antigen-binding fragment thereof, wherein
   the anti-c-Met antibody or an antigen-binding fragment thereof comprises
   a CDR-H1 comprising the amino acid sequence of SEQ ID NO: 4, a CDR-H2 comprising the amino acid sequence of SEQ ID NO: 5 or SEQ ID NO: 2, a CDR-H3 comprising the amino acid sequence of SEQ ID NO: 6 or SEQ ID NO: 3;
   a CDR-L1 comprising the amino acid sequence of SEQ ID NO: 7, a CDR-L2 comprising the amino acid sequence of SEQ ID NO: 8, and a CDR-L3 comprising the amino acid sequence of SEQ ID NO: 9 or SEQ ID NO: 15; and
   the anti-EGFR antibody or an antigen-binding fragment thereof comprises:
   a CDR-H1 comprising the amino acid sequence of SEQ ID NO: 109, a CDR-H2 comprising the amino acid sequence of SEQ ID NO: 110, a CDR-H3 comprising the amino acid sequence of SEQ ID NO: 111;
   a CDR-L1 comprising the amino acid sequence of SEQ ID NO: 112, a CDR-L2 comprising the amino acid sequence of SEQ ID NO: 113, and a CDR-L3 comprising the amino acid sequence of SEQ ID NO: 114.

5. The anti-c-Met/anti-EGFR bispecific antibody according to claim 4, wherein the antigen-binding fragment of the anti-c-Met antibody or the anti-EGFR antibody is selected from the group consisting of scFv, (scFv)2, scFvFc, Fab, Fab', and F(ab')2.

6. The anti-c-Met/anti-EGFR bispecific antibody according to claim 4, wherein the anti-c-Met antibody comprises:
   a CDR-H1 comprising the amino acid sequence of SEQ ID NO: 1, SEQ ID NO: 22, SEQ ID NO: 23, or SEQ ID NO: 24,
   a CDR-H2 comprising the amino acid sequence of SEQ ID NO: 2, SEQ ID NO: 25, or SEQ ID NO: 26,
   a CDR-H3 comprising the amino acid sequence of SEQ ID NO: 3, SEQ ID NO: 27, SEQ ID NO: 28,
   a CDR-L1 comprising the amino acid sequence of SEQ ID NO: 10, SEQ ID NO: 29, SEQ ID NO: 30, SEQ ID NO: 31, SEQ ID NO: 32, SEQ ID NO: 33, or SEQ ID NO: 106,
   a CDR-L2 comprising the amino acid sequence of SEQ ID NO: 11, SEQ ID NO: 34, SEQ ID NO: 35, or SEQ ID NO: 36, and
   a CDR-L3 comprising the amino acid sequence of SEQ ID NO: 12, SEQ ID NO: 13, SEQ ID NO: 14, SEQ ID NO: 15, SEQ ID NO: 16, SEQ ID NO: 37.

7. The anti-c-Met/anti-EGFR bispecific antibody according to claim 4, wherein the anti-c-Met antibody or the antigen-binding fragment thereof comprises:

a heavy chain variable region comprising the amino acid sequence of SEQ ID NO: 17, 74, 87, 90, 91, 92, 93, or 94, a light chain variable region comprising the amino acid sequence of SEQ ID NO: 18, 19, 20, 21, 75, 88, 95, 96, 97, 98, 99, 107, or 121, or a combination of the heavy chain variable region and the light chain variable region.

8. The anti-c-Met/anti-EGFR bispecific antibody according to claim 4, wherein the anti-c-Met antibody comprises:

a heavy chain comprising an amino acid sequence selected from the group consisting of SEQ ID NO: 62, the amino acid sequence from the $18^{th}$ to $462^{nd}$ positions of SEQ ID NO: 62, SEQ ID NO: 64, the amino acid sequence from the $18^{th}$ to $461^{st}$ positions of SEQ ID NO: 64, SEQ ID NO: 66, and the amino acid sequence from the $18^{th}$ to $460^{th}$ positions of SEQ ID NO: 66; and a light chain comprising the amino acid sequence selected from the group consisting of SEQ ID NO: 68, the amino acid sequence from the 20 to $240^{th}$ positions of SEQ ID NO: 68, SEQ ID NO: 70, the amino acid sequence from the 20 to $240^{th}$ positions of SEQ ID NO: 70, and SEQ ID NO: 108.

9. The anti-c-Met/anti-EGFR bispecific antibody according to claim 4, wherein the anti-EGFR antibody or the antigen-binding fragment thereof comprises:

a heavy chain variable region comprising the amino acid sequence of SEQ ID NO: 115 or SEQ ID NO: 117, a light chain variable region comprising the amino acid sequence of SEQ ID NO: 116 or SEQ ID NO: 118, or a combination thereof.

10. The anti-c-Met/anti-EGFR bispecific antibody according to claim 4, wherein the anti-EGFR antibody or the antigen-binding fragment thereof is linked to C-terminus of the anti-c-Met antibody.

11. A pharmaceutical composition comprising the anti-EGFR antibody or the antigen-binding fragment thereof of claim 1 and a pharmaceutically acceptable carrier.

12. A pharmaceutical composition comprising the anti-c-Met/anti-EGFR bispecific antibody of claim 4 and a pharmaceutically acceptable carrier.

13. The anti-c-Met/anti-EGFR bispecific antibody according to claim 4, wherein the anti-c-Met antibody or the antigen-binding fragment thereof comprises:

a heavy chain variable region comprising the amino acid sequence of SEQ ID NO: 17, 74, 87, 90, 91, 92, 93, or 94, and a light chain variable region comprising the amino acid sequence of SEQ ID NO: 18, 19, 20, 21, 75, 88, 95, 96, 97, 98, 99, 107, or 121;

and the anti-EGFR antibody or the antigen-binding fragment thereof comprises:

a heavy chain variable region comprising the amino acid sequence of SEQ ID NO: 115 or SEQ ID NO: 117, and a light chain variable region comprising the amino acid sequence of SEQ ID NO: 116 or SEQ ID NO: 118.

* * * * *